(12) United States Patent
Iwase

(10) Patent No.: US 10,916,012 B2
(45) Date of Patent: Feb. 9, 2021

(54) IMAGE PROCESSING APPARATUS AND IMAGE PROCESSING METHOD

(71) Applicant: CANON KABUSHIKI KAISHA, Tokyo (JP)

(72) Inventor: Yoshihiko Iwase, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 74 days.

(21) Appl. No.: 15/724,065

(22) Filed: Oct. 3, 2017

(65) Prior Publication Data

US 2018/0096479 A1 Apr. 5, 2018

(30) Foreign Application Priority Data

Oct. 5, 2016 (JP) .................... 2016-196895
Jul. 21, 2017 (JP) .................... 2017-141772

(51) Int. Cl.
*G06T 7/00* (2017.01)
*A61B 3/10* (2006.01)
(Continued)

(52) U.S. Cl.
CPC .......... *G06T 7/0016* (2013.01); *A61B 3/0025* (2013.01); *A61B 3/0041* (2013.01); *A61B 3/102* (2013.01); *A61B 3/14* (2013.01); *G06T 7/0012* (2013.01); *G06T 7/12* (2017.01); *G06T 7/13* (2017.01); *G06T 7/136* (2017.01); *G06T 7/60* (2013.01); *G06T 2207/10101* (2013.01);
(Continued)

(58) Field of Classification Search
CPC ....... A61B 3/14; A61B 3/0041; A61B 3/0025; A61B 3/102; G06T 2207/30041; G06T 2207/10101; G06T 7/0016; G06T 7/12; G06T 7/136; G06T 7/0012; G06T 2207/20036; G06T 2207/20044; G06T 7/13; G06T 7/60
See application file for complete search history.

(56) References Cited

U.S. PATENT DOCUMENTS

2011/0141259 A1* 6/2011 Nakano ................ A61B 3/0025
  348/78
2012/0113390 A1* 5/2012 Torii ..................... A61B 3/024
  351/208
(Continued)

FOREIGN PATENT DOCUMENTS

JP  2011-515194 A  5/2011
JP  2015-029558 A  2/2015
(Continued)

OTHER PUBLICATIONS

Park et al. "Posterior Precortical Vitreous Pocket in Children." Current Eye Research, vol. 40, issue 10, Oct. 20, 2014, pp. 1034-1039 (Year: 2014).*

*Primary Examiner* — Jon Chang
(74) *Attorney, Agent, or Firm* — Canon U.S.A., Inc. IP Division

(57) ABSTRACT

An image processing apparatus includes an acquisition unit configured to acquire a tomographic image of at least a retina and a vitreous body of a subject's eye, and a detection unit configured to detect, based on an intensity value of the tomographic image, an outer edge of the vitreous body in a region located on a vitreous body side of a region regarding the retina in the tomographic image.

28 Claims, 17 Drawing Sheets

(51) Int. Cl.
*A61B 3/00* (2006.01)
*G06T 7/13* (2017.01)
*G06T 7/60* (2017.01)
*A61B 3/14* (2006.01)
*G06T 7/12* (2017.01)
*G06T 7/136* (2017.01)

(52) U.S. Cl.
CPC ............... *G06T 2207/20036* (2013.01); *G06T 2207/20044* (2013.01); *G06T 2207/30041* (2013.01)

(56) References Cited

U.S. PATENT DOCUMENTS

| | | | |
|---|---|---|---|
| 2012/0249962 A1* | 10/2012 | Uchida | A61B 3/102 351/208 |
| 2013/0003017 A1* | 1/2013 | Muto | A61B 3/102 351/206 |
| 2013/0058553 A1* | 3/2013 | Yonezawa | G06K 9/0061 382/131 |
| 2017/0164825 A1* | 6/2017 | Chen | A61B 3/102 |

FOREIGN PATENT DOCUMENTS

| | | |
|---|---|---|
| JP | 2014203901 A1 | 2/2017 |
| WO | 2014/203901 A1 | 12/2014 |

* cited by examiner

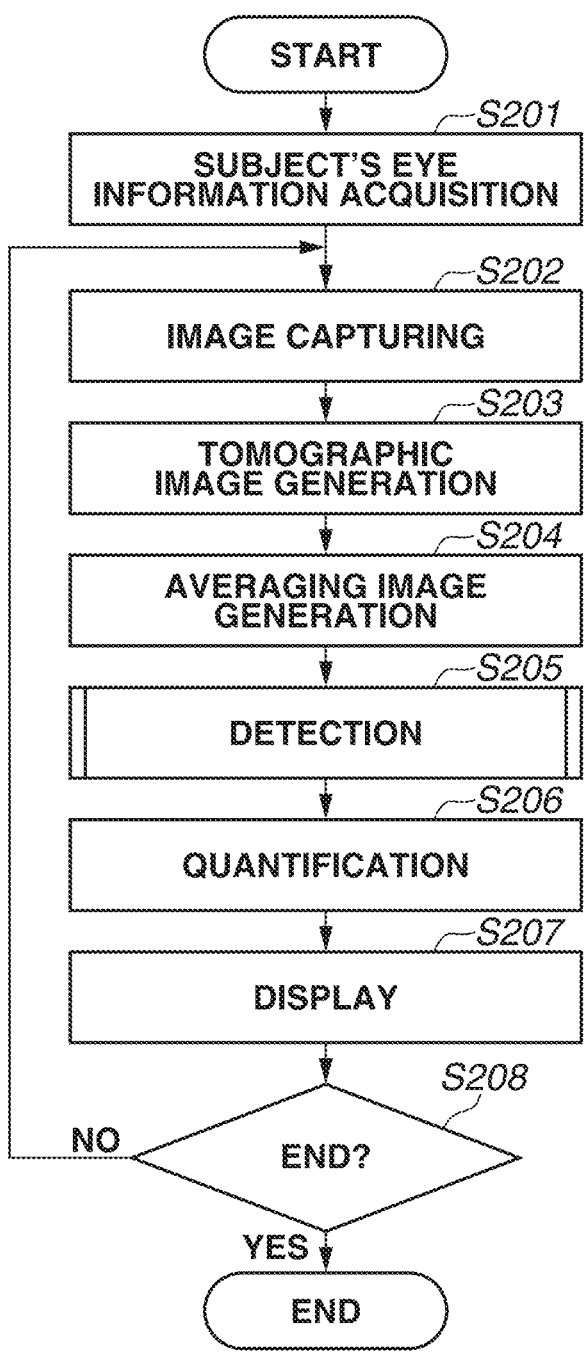
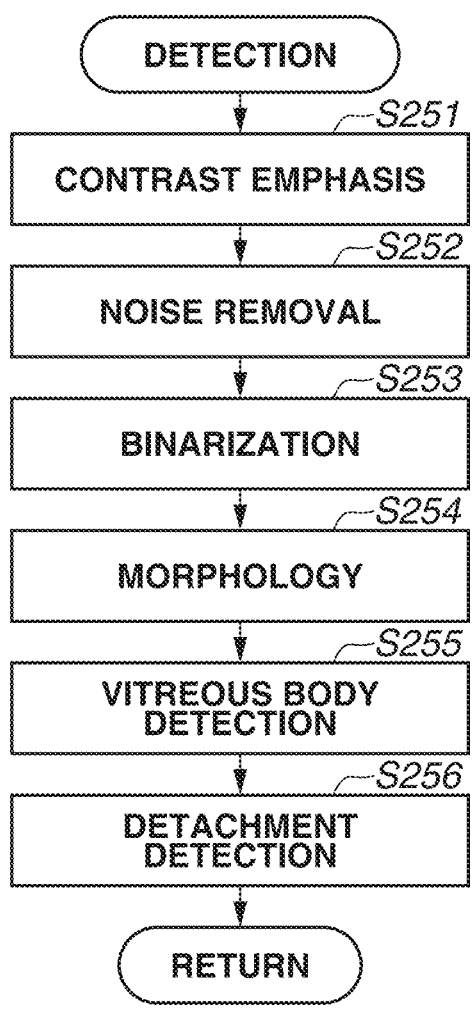

1001

1002

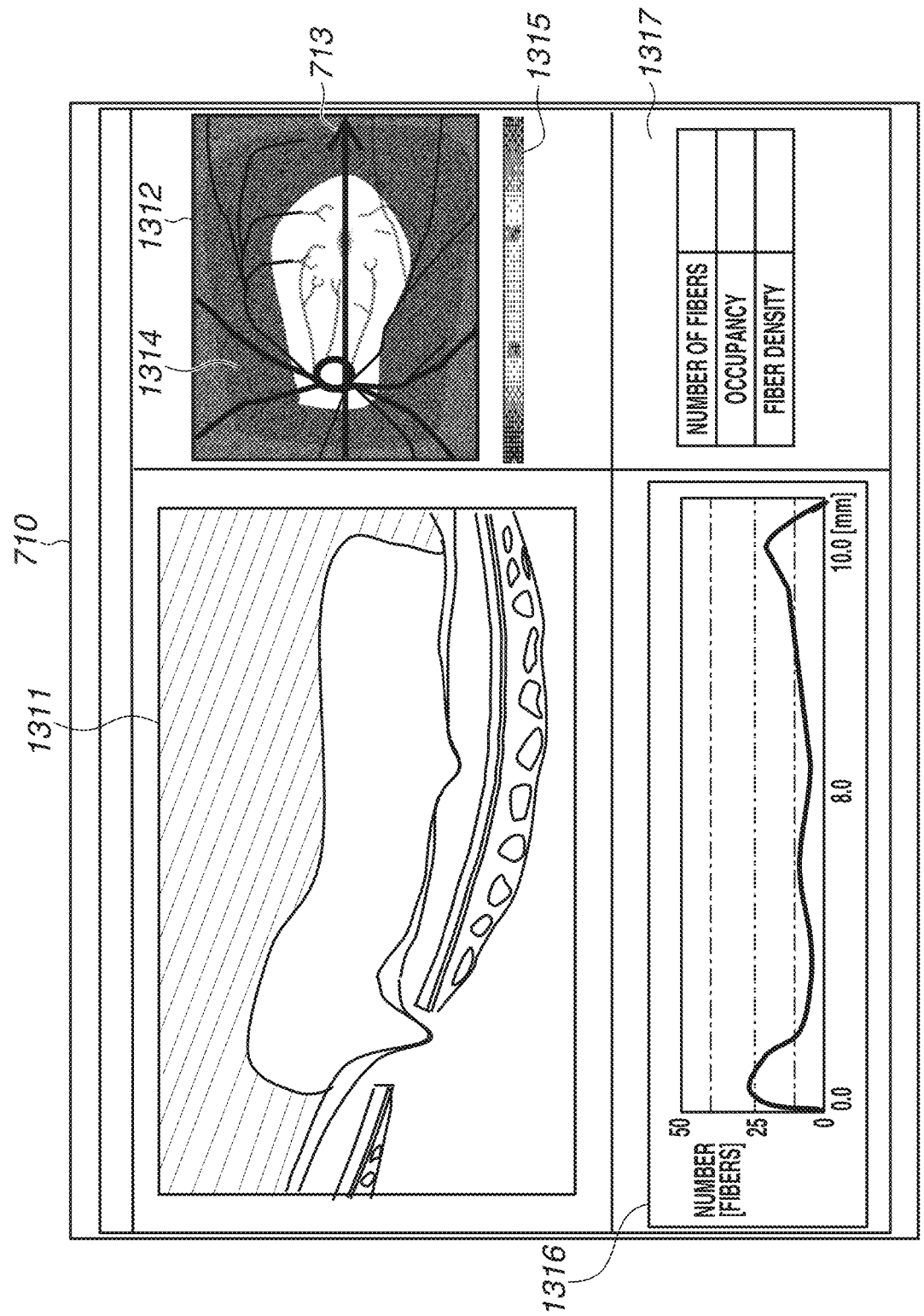

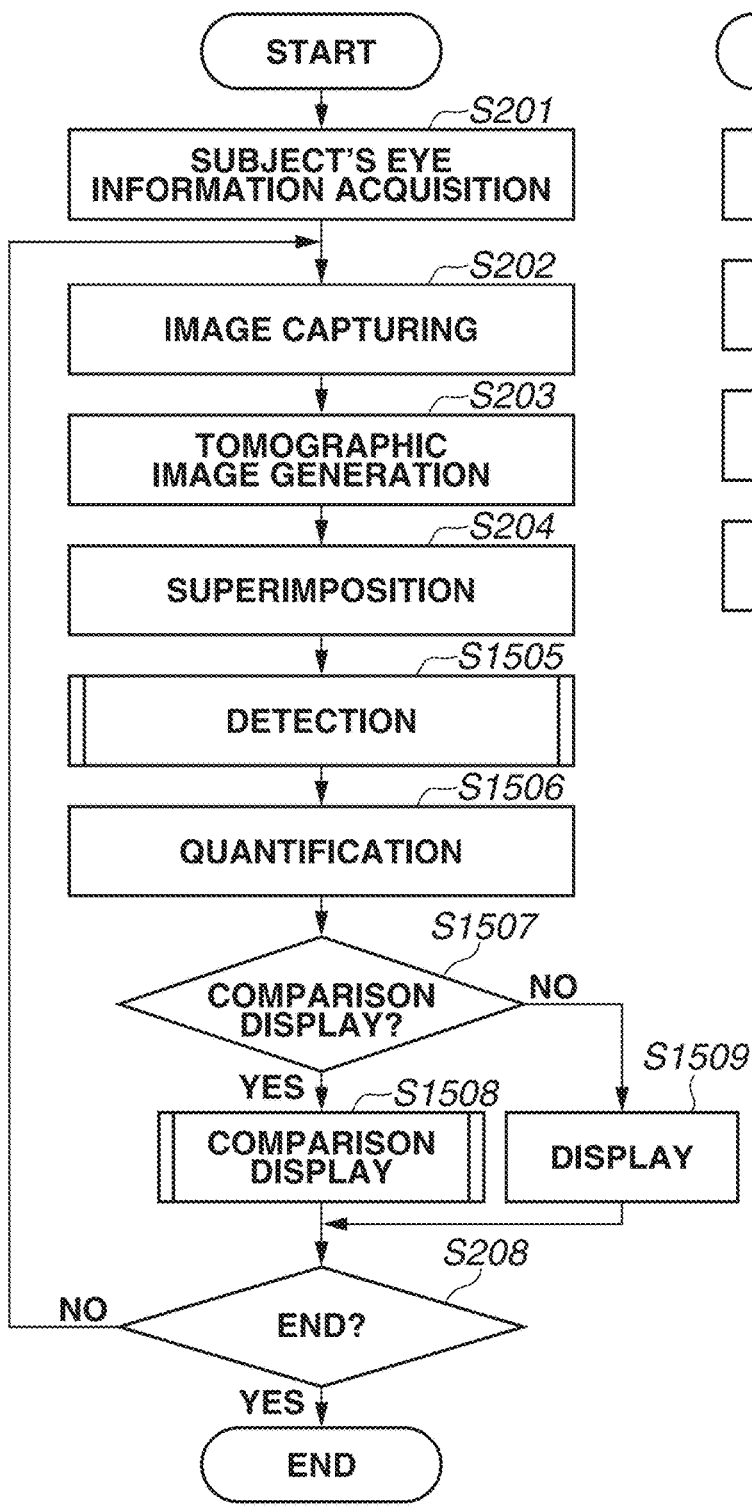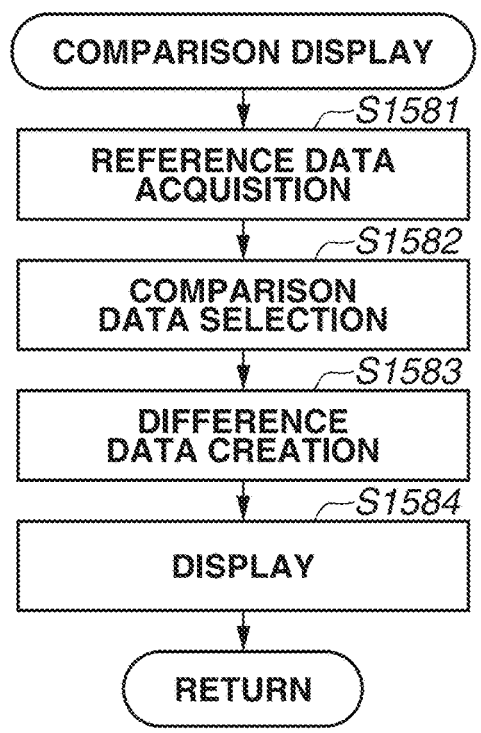

IMAGE PROCESSING APPARATUS AND IMAGE PROCESSING METHOD

BACKGROUND

Field of the Disclosure

The present disclosure relates to an image processing apparatus and an image processing method for processing a tomographic image of a subject's eye.

Description of the Related Art

A tomographic image capturing apparatus for an eye portion, such as optical coherence tomography (OCT), can three-dimensionally observe the state of the inside of retinal layers. In recent years, this tomographic image capturing apparatus attracts attention because the tomographic image capturing apparatus is useful to more accurately diagnose a disease. As a form of the OCT, for example, there is time domain OCT (TD-OCT) constructed by combining a broadband light source and a Michelson interferometer. This TD-OCT is configured to scan the delay of a reference arm to measure light interfering with backscattered light of a signal arm, thereby obtaining information of depth resolution. It is, however, difficult to acquire an image at high speed using such TD-OCT. Thus, as a method for acquiring an image at higher speed, spectral domain OCT (SD-OCT) is known as OCT for acquiring an interferogram with a spectrometer, using a broad-band light source. Further, swept-source OCT (SS-OCT) based on a technique for using a high-speed wavelength-swept light source as a light source to measure spectral interference with a single-channel photodetector is known. Further, in recent years, not only the retina but also the vitreous body can be viewed due to the advancement of OCT.

The publication of Japanese Translation of PCT International Application No. 2011-515194 discusses a technique for using a histogram of an intensity value within the vitreous body in a tomographic image of the fundus obtained by OCT, thereby evaluating large and bright macula within the vitreous body as an indication of the possibility of uveitis.

SUMMARY

According to an aspect of the present invention, an image processing apparatus includes an acquisition unit configured to acquire a tomographic image of at least a retina and a vitreous body of a subject's eye, and a detection unit configured to detect, based on an intensity value of the tomographic image, an outer edge of the vitreous body in a region located on a vitreous body side of a region regarding the retina in the tomographic image.

Further features of the present invention will become apparent from the following description of exemplary embodiments with reference to the attached drawings.

BRIEF DESCRIPTION OF THE DRAWINGS

FIGS. 2A and 2B are flowcharts illustrating a flow of processing in the image processing system.

FIG. 13 is an example of a display screen of a display unit of the image processing system.

FIGS. 15A and 15B are flowcharts illustrating a flow of processing of the image processing system.

DESCRIPTION OF THE EMBODIMENTS

The vitreous cortex may be detached from the retina with aging. At this time, the retina may be pulled by the vitreous body, and a macular hole may be caused. Further, inflammation may be caused in the retina or the choroid, whereby opacity may be caused in the vitreous body. As described above, due to a change in the vitreous body, a disease may be caused in the retina, or a disease may be caused in the vitreous body itself. When treating such a disease, it is expected that a doctor can quantitatively recognize the state of the vitreous body before surgery.

One of aspects of the present invention is to enable a user to quantitatively recognize the structure of the vitreous body in a tomographic image obtained by optical coherence tomography (OCT).

Therefore, one of image processing apparatuses according to the present exemplary embodiment detects, in a tomographic image including the retina and the vitreous body of a subject's eye, the outer edge of the vitreous body in a region on the vitreous body side of a region regarding the retina, based on a luminance value (an intensity value) of the tomographic image. This enables the user to quantitatively recognize the structure of the vitreous body in a tomographic image obtained by OCT.

Figure 3A:
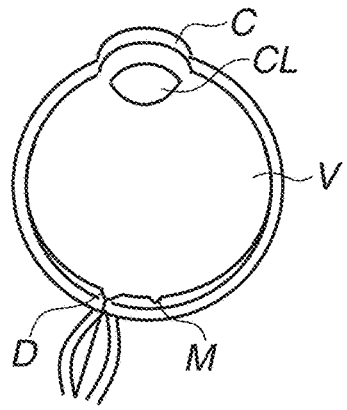
FIGS. 3A, 3B, and 3C are diagrams illustrating a structure of an eye portion, a tomographic image, and a fundus image, respectively.
Figure 3B:
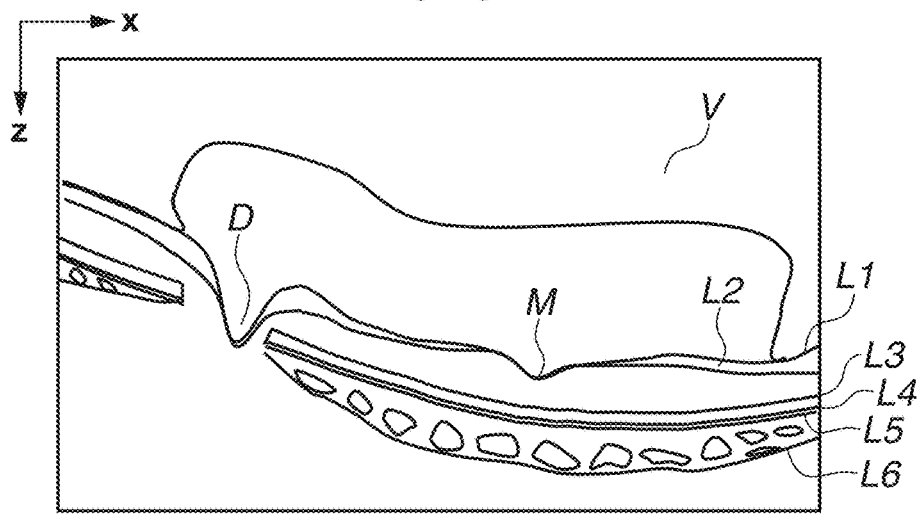
Figure 3C:
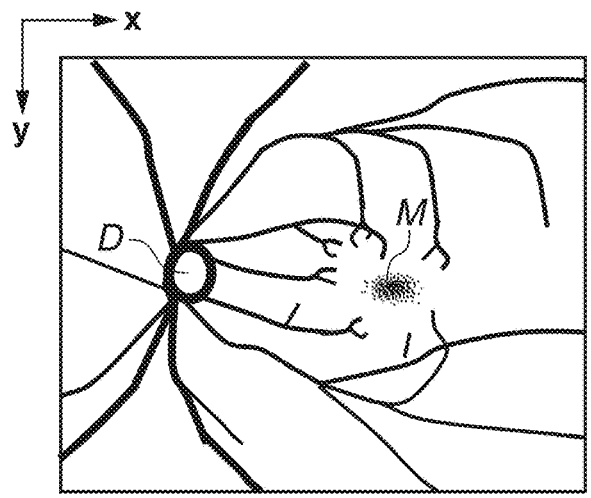

With reference to the drawings, a first exemplary embodiment is described below. An image processing system including an image processing apparatus according to the present exemplary embodiment is characterized in detecting the vitreous body from a tomographic image. A description is given below of the details of the image processing system including the image processing apparatus according to the present exemplary embodiment, the structure of an eye, and images of an eye acquired by the image processing system. FIGS. 3A to 3C are diagrams illustrating the structure and images of an eye acquired by the image processing system. FIG. 3A illustrates a schematic diagram of an eyeball. FIG. 3A illustrates the cornea C, the crystalline lens CL, the vitreous body V, a macular portion M (a center portion of the macula represents the central fovea), and an optic disc portion D. A case is described where a tomographic image capturing apparatus 200 according to the present exemplary embodiment mainly captures a posterior portion of the retina including the vitreous body, the macular portion, and the optic disc portion. The tomographic image capturing apparatus 200 can also capture an anterior eye portion including the cornea and the crystalline lens.

Figure 1:
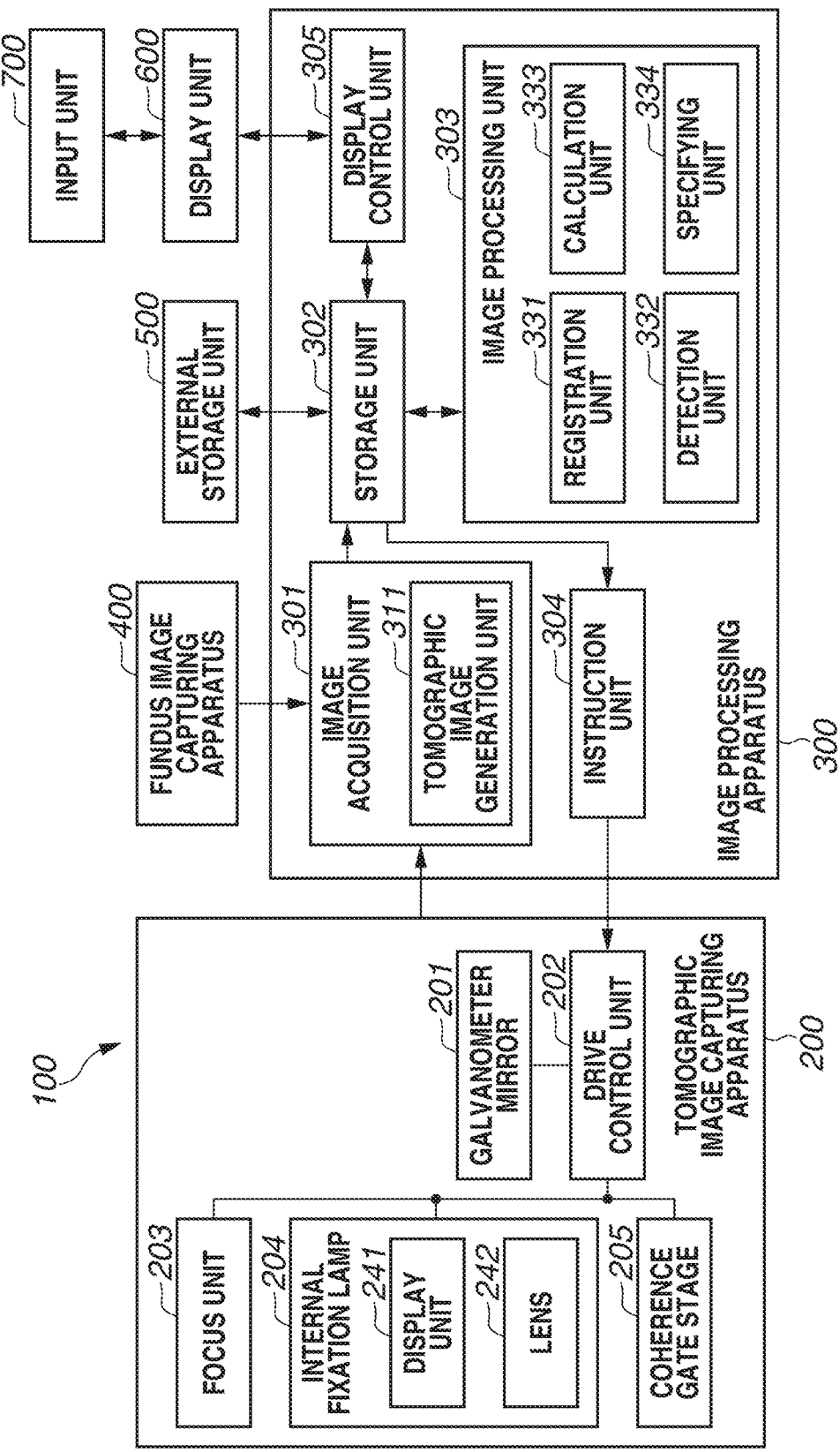
FIG. 1 is a block diagram illustrating a configuration of an image processing system.

First, FIG. 1 is a block diagram illustrating the configuration of an image processing system 100, which includes an image processing apparatus 300 according to the present exemplary embodiment. As illustrated in FIG. 1, the image processing system 100 is configured by connecting the image processing apparatus 300 to a tomographic image capturing apparatus (also referred to as "OCT") 200, a fundus image capturing apparatus 400, an external storage unit 500, a display unit 600, and an input unit 700 via interfaces. The tomographic image capturing apparatus 200 is an apparatus for capturing a tomographic image of an eye portion. An apparatus used as the tomographic image capturing apparatus 200 is, for example, spectral domain optical coherence tomography (SD-OCT) or swept-source optical coherence tomography (SS-OCT). The tomographic image capturing apparatus 200 is a known apparatus and therefore is not described in detail, and a description is given of the capturing of a tomographic image performed according to an instruction from the image processing apparatus 300.

Further, a galvanometer mirror 201 scans the fundus with measurement light and defines the image capturing range of the fundus to be captured by the OCT. Further, a drive control unit 202 controls the driving range and the speed of the galvanometer mirror 201, thereby defining the image capturing range and the number of scan lines in a planar direction (the scanning speed in the planar direction) of the fundus. For ease of description, the galvanometer mirror 201 is illustrated as a single unit, but actually includes two mirrors (X-scan mirror and Y-scan mirror). Thus, the galvanometer mirror 201 can scan a desired range on the fundus with measurement light.

Further, a focus unit 203 focuses on retinal layers of the fundus through an anterior eye portion of an eye as a subject. Measurement light is focused by a focus lens (not illustrated) on the retinal layers of the fundus through the anterior eye portion of the eye as the subject. The measurement light emitted to the fundus is reflected and scattered by each retinal layer and returns. In a case where the vitreous body is observed in detail, the focus unit 203 is moved further on the anterior eye portion side than the retinal layers and focuses on the vitreous body.

Further, an internal fixation lamp 204 includes a display unit 241 and a lens 242. As the display unit 241, a display unit is used in which a plurality of light-emitting diodes (LEDs) are arranged in a matrix. The lighting positions of the LEDs are changed by the control of the drive control unit 202 according to a part to be captured. Light from the display unit 241 is guided to the subject's eye through the lens 242. The light emitted from the display unit 241 has a wavelength of 520 nm, and a desired pattern is displayed by the drive control unit 202.

Further, a coherence gate stage 205 is controlled by the drive control unit 202 to deal with the difference in the eye axial length of the subject's eye. A "coherence gate" refers to a position where the optical distances of measurement light and reference light in the OCT are equal to each other. Further, as an image capturing method, the position of the coherence gate is controlled, thereby controlling the capturing of the retinal layer side or a side deeper than the retinal layers. With reference to FIG. 3B, a description is given of a tomographic image acquired by the tomographic image capturing apparatus 200. FIG. 3B illustrates the vitreous body V, a macular portion M, and an optic disc portion D. Further, FIG. 3B illustrates a boundary L1 between the internal limiting membrane (ILM) and the nerve fiber layer (NFL), a boundary L2 between the NFL and the ganglion cell layer (GCL), the photoreceptor cell inner segment/outer segment junction (ISOS) L3, the retinal pigment epithelium layer (RPE) L4, the Bruch's membrane (BM) L5, and the choroid L6. In the tomographic image, the horizontal axis (main scanning direction of the OCT) is an x-axis, and the vertical axis (depth direction) is a z-axis.

The tomographic image capturing apparatus 200 includes a light reception unit (not illustrated) for receiving light obtained by multiplexing return light from the subject's eye irradiated with measurement light, with reference light corresponding to the measurement light. Further, the image processing apparatus 300 is connected to the tomographic image capturing apparatus 200 so that the image processing apparatus 300 can communicate with the tomographic image capturing apparatus 200. The image processing apparatus 300 acquires a tomographic image based on the light reception result of the light reception unit. Alternatively, the image processing apparatus 300 may be configured in an integrated manner within the tomographic image capturing apparatus 200.

The fundus image capturing apparatus 400 is an apparatus for capturing a fundus image of an eye portion. Examples of the apparatus include a fundus camera and a scanning laser ophthalmoscope (SLO). FIG. 3C illustrates a fundus image of an eye portion. FIG. 3C illustrates a macular portion M and an optic disc portion D. Thick curved lines represent the blood vessels of the retina. In the fundus image, the horizontal axis (main scanning direction of the OCT) is an x-axis, and the vertical axis (sub-scanning direction of the OCT) is a y-axis. The tomographic image capturing apparatus 200 and the fundus image capturing apparatus 400 may be configured in an integrated manner or in a separate manner.

Further, the image processing apparatus 300 includes an image acquisition unit 301, a storage unit 302, an image processing unit 303, an instruction unit 304, and a display control unit 305. The image acquisition unit 301 includes a tomographic image generation unit 311. The image acquisition unit 301 acquires signal data of a tomographic image captured by the tomographic image capturing apparatus 200 and performs signal processing, thereby generating a tomographic image. Further, the image acquisition unit 301 acquires fundus image data captured by the fundus image capturing apparatus 400. Then, the image acquisition unit 301 stores the generated tomographic image and the fundus image in the storage unit 302. The image processing unit 303 includes a registration unit 331, a detection unit 332, a calculation unit 333, and a specifying unit 334. The registration unit 331 performs tomographic image registration between a plurality of tomographic images and performs registration between a tomographic image and a fundus image. The detection unit 332 detects a vitreous boundary and a vitreous region. The calculation unit 333 obtains the numerical value of a feature regarding a region defined by the vitreous boundary and the upper layer of the retina. The specifying unit 334 specifies a region to be calculated by the calculation unit 333.

Further, the external storage unit 500 holds information (name, age, and gender of a patient) regarding the subject's eye, captured image data, image capturing parameters, image analysis parameters, and parameters set by an operator in association with each other.

Further, the input unit 700 is, for example, a mouse, a keyboard, or a touch operation screen. The operator gives an instruction to the image processing apparatus 300, the tomographic image capturing apparatus 200, and the fundus image capturing apparatus 400 through the input unit 700.

Next, with reference to FIGS. 2A and 2B, the processing procedure of the image processing apparatus 300 according to the present exemplary embodiment is described. FIG. 2A is a flowchart illustrating the flow of the operation processing of the whole system according to the present exemplary embodiment.

<Step S201: Subject's Eye Information Acquisition>

In step S201, a subject's eye information acquisition unit (not illustrated) externally acquires a subject identification number as information identifying a subject's eye. Then, based on the subject identification number, the subject's eye information acquisition unit acquires information regarding the subject's eye held in the external storage unit 500 and stores the acquired information in the storage unit 302.

<Step S202: Image Capturing>

In step S202, the tomographic image capturing apparatus 200 scans the subject's eye, thereby capturing images. The subject's eye is scanned as follows. If the operator selects the start of scanning (not illustrated), the tomographic image capturing apparatus 200 controls the drive control unit 202 to cause the galvanometer mirror 201 to operate, thereby scanning tomographic images. The galvanometer mirror 201 includes an X-scanner for the horizontal direction and a Y-scanner for the vertical direction. Thus, if the directions of these scanners are changed, it is possible to perform scanning in the horizontal direction (X) and the vertical direction (Y) in an apparatus coordinate system. Then, the directions of these scanners are simultaneously changed, whereby it is possible to perform scanning in a direction obtained by combining the horizontal direction and the vertical direction. Thus, it is possible to perform scanning in any direction on a fundus plane.

To start imaging, various image capturing parameters are adjusted. More specifically, at least the position of the internal fixation lamp 204, a scan range, a scan pattern, the position of the coherence gate, and focus are set. The drive control unit 202 controls the LEDs of the display unit 241 and controls the position of the internal fixation lamp 204 so that the center of a macular portion and the optic disc can be captured. As the scan pattern, a scan pattern such as a raster scan for capturing a three-dimensional volume, a radial scan, or a cross scan is set. In each scan pattern, it is desirable to repeatedly capture a plurality of images (N>2) on a single line. The description is given on the assumption that the position of the coherence gate is on the vitreous body side, and images are captured also by focusing on the vitreous body. After the adjustment of these image capturing parameters is completed, the operator selects a start of capturing images (not illustrated), thereby capturing images.

<Step S203: Tomographic Image Generation>

In step S203, the tomographic image generation unit 311 generates tomographic images. The tomographic image generation unit 311 performs a general reconfiguration process on each interference signal, thereby generating a tomographic image. First, the tomographic image generation unit 311 removes fixed-pattern noise from the interference signal. The fixed-pattern noise is removed by averaging a plurality of detected A-scan signals to extract fixed-pattern noise and subtracting the extracted fixed-pattern noise from the input interference signal. Next, the tomographic image generation unit 311 performs a desired window function process to optimize the depth resolution and the dynamic range, which have a trade-off relationship when subjected to the Fourier transform at finite intervals. Next, the tomographic image generation unit 311 performs a fast Fourier transform (FFT) process, thereby generating a tomographic signal.

<Step S204: Addition Averaging Image Generation>

In step S204, the registration unit 331 performs registration between the tomographic images generated by repeatedly capturing a plurality of images on a single line in step S203. As the registration process, for example, an evaluation function representing the degree of similarity between two tomographic images is defined in advance, and the above tomographic images are deformed so that the evaluation function has the best value. Examples of the evaluation function include a method for making an evaluation based on pixel values (e.g., a method for making an evaluation using a correlation coefficient). An expression in a case where a correlation coefficient is used as the evaluation function representing the degree of similarity is illustrated by expression (1).

$$\frac{\int\int_S (f(x,z) - \bar{f})(g(x,z) - \bar{g}) dx dz}{\sqrt{\int\int_S (f(x,z) - \bar{f})^2 dx dz \int\int_S (g(x,z) - \bar{g})^2 dx dz}} \quad (1)$$

In expression (1), the region of a first tomographic image is f(x, z), and the region of a second tomographic image is g(x, z).

$$\bar{f}, \bar{g} \quad (2)$$

In expression (2), these values represent the averages of the region f(x, z) and the region g(x, z). Each region is an image region for use in the registration. Normally, a region having a size smaller than or equal to a tomographic image is set as the region. In a tomographic image of an eye, it is desirable that the region should be set to include a retinal layer region. Examples of the image deformation process include the process of performing translation or rotation using affine transformation, and the process of changing the enlargement ratio.

Further, as the registration process, positions may be adjusted based on feature points. For example, features such as retinal layers and a lesion may be extracted from two-dimensional tomographic images. Using these extraction results, the registration may be performed by selecting stably detected feature points. Alternatively, a layer boundary line may be detected from tomographic images, and the registration may be performed based on the detected layer boundary line. The registration process is not limited to a single method, and may be performed by combining the above methods.

The registration unit 331 performs addition averaging on pixels at the same coordinates on the plurality of tomographic images subjected to the registration, thereby generating a single tomographic image subjected to the addition averaging from the plurality of tomographic images. This process is executed on a plurality of tomographic images on each line. By performing the addition averaging process, a high-quality image in which noise is reduced and signals of the vitreous body and the retina are emphasized, can be generated.

This process is described using an example where images are captured by a cross scan. Suppose that in the cross scan, the number of lines is two, and 100 tomographic images are repeatedly captured on each line. In this case, when images are captured, a total of 200 pieces of tomographic image data are acquired. After the process of step S204, however, two pieces of tomographic image data subjected to the addition averaging process are obtained. In other words, the number of pieces of tomographic image data is equal to the number of lines.

<Step S205: Detection>

In step S205, the detection unit 332 detects the vitreous body. With reference to a flowchart in FIG. 2B and FIGS. 4A, 4B, 5A, 5B, and 5C, the processing of the detection unit 332 is described.

<Step S251: Contrast Emphasis>

Figure 4A:
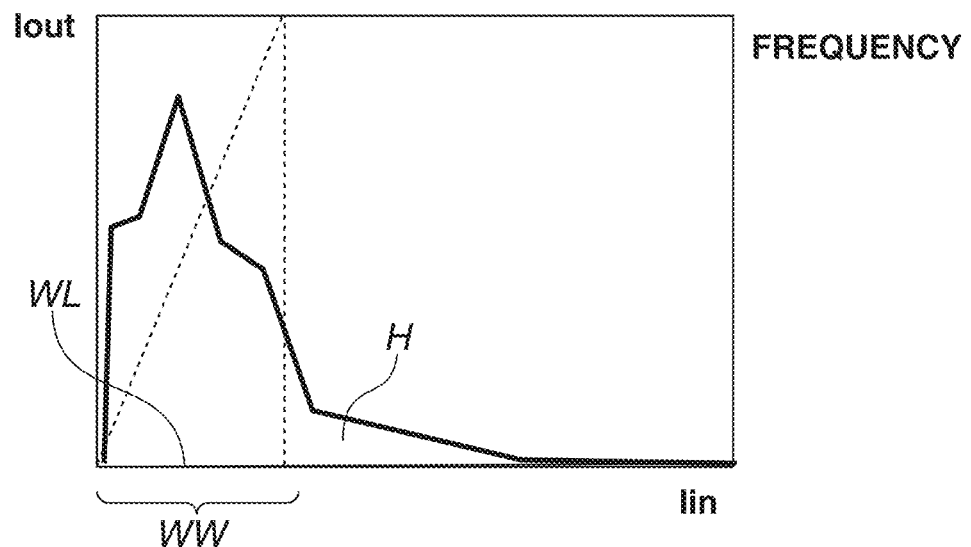
FIGS. 4A and 4B are diagrams illustrating processing of an image processing apparatus.
Figure 4B:
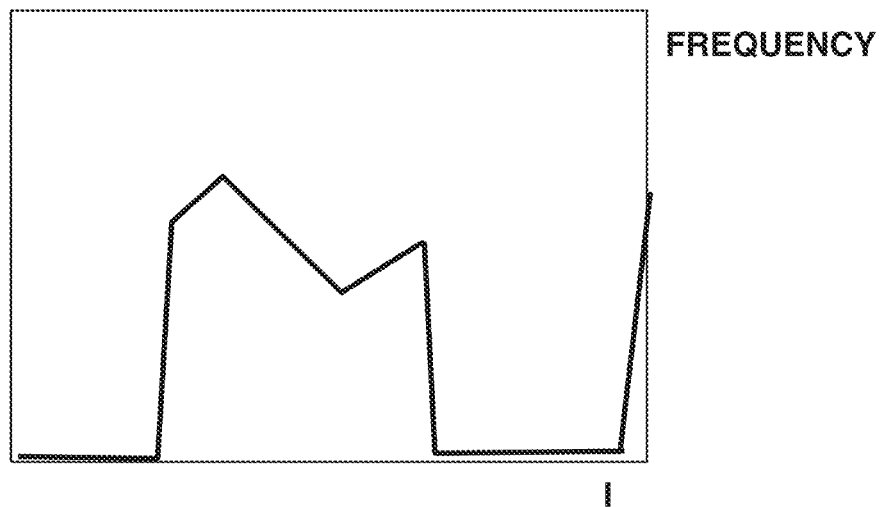

In step S251, the detection unit 332 emphasizes the contrast of the tomographic image generated in steps S203 and S204. In the tomographic image, the vitreous body has a luminance value (an intensity value) lower than that of the retina. Therefore, in this process, the process of heightening a luminance value indicating low luminance is performed to emphasize a vitreous region. With reference to FIGS. 4A and 4B, this process is described. FIG. 4A illustrates a luminance histogram (region H indicated by a solid line in FIG. 4A) of the tomographic image, and a window width (WW) and a window level (WL) for the contrast emphasis. The horizontal axis represents a luminance value (Iin), and the vertical axis represents a luminance value (Iout) of an output image and the frequency of the luminance histogram. The WW is the range of a luminance value for emphasizing the contrast, and the WL is a center luminance value of the range where the contrast is emphasized. FIG. 4B illustrates an example of a histogram after the process of heightening the luminance value indicating low luminance as illustrated in FIG. 4A is performed. In FIG. 4B, the horizontal axis represents a luminance value (I), and the vertical axis represents the frequency of the luminance histogram. As illustrated in FIG. 4B, the luminance value indicating low luminance becomes high. By this process, the luminance of the vitreous region is emphasized. Since the luminance value of a retinal region is originally high, the overall luminance value is a high value. In FIGS. 4A and 4B, a transformation curve for the contrast emphasis is illustrated as a straight line, but is not limited to this. Alternatively, another transformation curve such as a gamma curve or a sigmoid curve may be used.

<Step S252: Noise Removal>

In step S252, the detection unit 332 removes noise from the tomographic image of which the low luminance region is subjected to the contrast emphasis. As the noise removal, for example, a median filter or a Gaussian filter is used. The detection unit 332 may change the size of the filter for use in the noise removal according to the amount of noise. In this case, the amount of noise is determined by setting, as a region where the retina or the vitreous body is not present, a rectangular region of any size in a region below the choroid L6, evaluating the variance and the standard deviation of luminance values in the rectangular region, and evaluating noise. In this case, it is possible to estimate that as the numerical value of the variance or the standard deviation is larger, the noise is larger. Alternatively, the amount of noise may be determined based on the number of the tomographic images subjected to the addition averaging in step S204. In this case, it is possible to estimate that as the number of the averaged tomographic images is smaller, the noise is larger, and as the number of the averaged tomographic images is larger, the noise is smaller. Then, if the amount of noise is large, the filter size is set to be large. If the amount of noise is small, the filter size is set to be small. Consequently, it is possible to reduce an image blur due to the noise removal, and remove noise if the amount of noise is large. Further, it is desirable to determine the upper limit of the filter size based on the physical size of each pixel. An image range corresponding to a pixel in an image differs between, for example, a case where the image is captured by 100 A-scans in the range of 1 mm and a case where the image is captured by 50 A-scans in the range of 1 mm. More specifically, in a case where a parameter for the noise removal filter in the X-direction is set to 10, the physical size of each pixel in an image captured by 100 A-scans is equivalent to 0.1 mm, but the physical size of each pixel in an image captured by 50 A-scans is equivalent to 0.2 mm. Thus, the parameter is adjusted so that noise is removed in a similar range. The order of the processes of steps S251 and S252 may be reversed.

<Step S253: Binarization>

In step S253, the detection unit 332 performs binarization. As a method for the binarization, in a case where the range of the luminance value of the vitreous body after the contrast emphasis is known from the apparatus characteristics, a fixed threshold may be used. Alternatively, a threshold may be dynamically determined by a percentile method or a discrimination analysis method. The vitreous body and the retinal region are detected by the binarization.

<Step S254: Morphological Process>

In step S254, the detection unit 332 performs a morphological process. As a result of the binarization process, a hole may be caused in a part of the vitreous region having low luminance, or local noise may remain in a part of the vitreous region. This process is performed to integrate or remove these parts. Morphology uses dilation for expanding a region and erosion for contracting a region, in combination. In the combination of these processes, the execution of dilation after erosion is also referred to as "opening", and the execution of erosion after dilation is also referred to as "closing". By this process, a hole is filled and noise is removed in the vitreous body and the retinal region binarized in step S253.

Figure 5A:
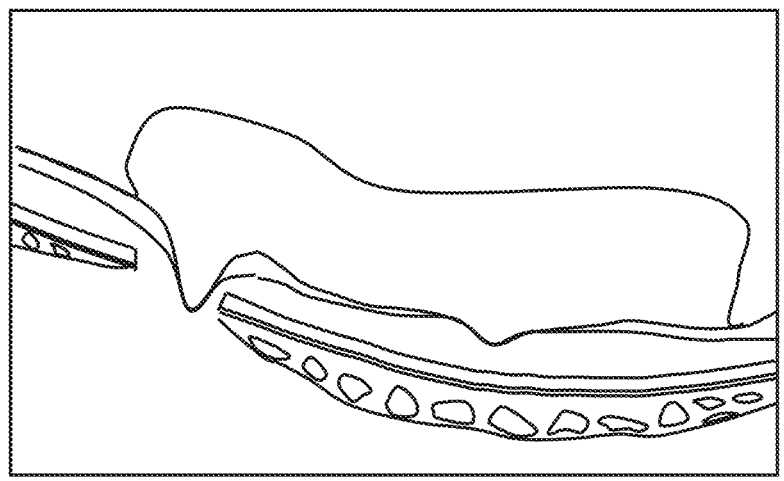
FIGS. 5A, 5B, and 5C are diagrams illustrating the processing of the image processing apparatus.
Figure 5B:
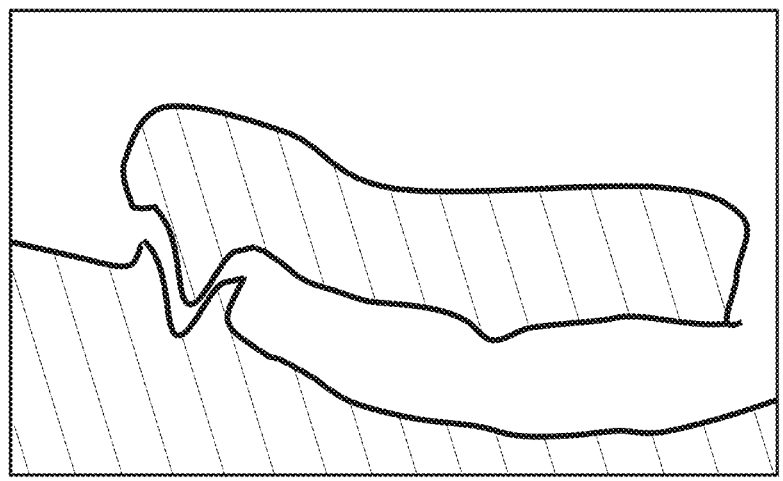
Figure 5C:
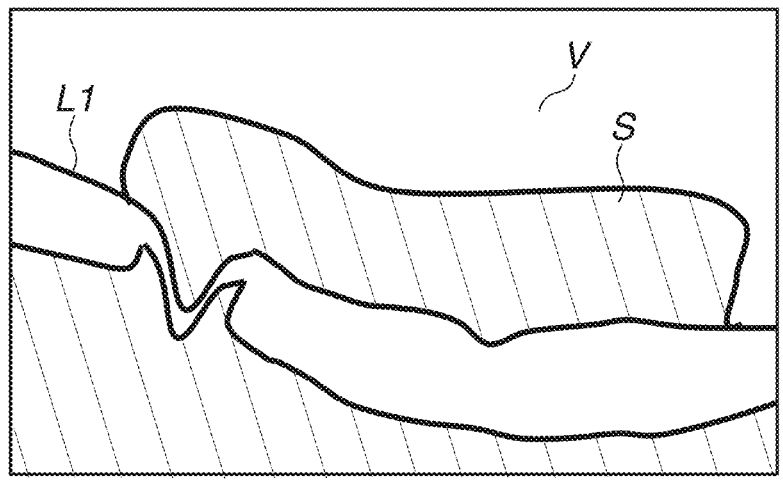

FIGS. 5A to 5C illustrate examples of the tomographic image subjected to the processes of steps S251 to S254. FIG. 5A illustrates the tomographic image created up to step S204, i.e., an input image input to the detection unit 332. FIG. 5B illustrates the tomographic image subjected to the processing by the detection unit 332. As illustrated in FIG. 5B, the tomographic image is divided into the vitreous region and the retinal region (white region in FIG. 5B) and background regions (shaded regions in FIG. 5B). This process is an example of a technique in which the detection unit 332 detects, based on the luminance value (the intensity value) of the tomographic image, the outer edge (boundary) of the vitreous body in a region further on the vitreous body side than a region regarding the retina in a tomographic image. Alternatively, another technique may be used so long as the technique is based on the luminance value of a tomographic image. The "outer edge of the vitreous body" refers to the boundary between the vitreous body and a detachment region (a posterior vitreous pocket) of the vitreous body.

<Step S255: Vitreous Body Detection>

In step S255, the detection unit 332 detects a vitreous boundary. In the detection of the vitreous boundary, a boundary line tracking process is performed on the binarized regions in the binarized image, thereby obtaining the boundary lines of the regions. Consequently, it is possible to detect the boundary lines of the regions as indicated by thick solid lines in FIG. 5B.

Further, the detection unit 332 detects a boundary L1 between the ILM and the NFL from the tomographic image illustrated in FIG. 5A. In other words, the detection unit 332 detects a region regarding the retina in the tomographic image. For example, the detection unit 332 applies a median filter and a Sobel filter to the tomographic image, thereby creating images (hereinafter referred to as a "median image" and a "Sobel image"). Next, the detection unit 332 creates a profile with respect to each A-scan from the created median image and Sobel image. From the median image, a profile of luminance values is obtained. From the Sobel image, a profile of slopes is obtained. Then, the detection unit 332 detects peaks in the profile created from the Sobel image. The detection unit 332 refers to the profile of the median image corresponding to luminance values before and after a detected peak and a luminance value between detected peaks, thereby detecting a retinal layer boundary. FIG. 5C illustrates an image obtained by integrating the boundary lines detected by this process and the boundary lines detected in FIG. 5B. As illustrated in FIG. 5C, if the position of the retina is specified, a region above the retina is the vitreous body V. Thus, it is possible to obtain the region of the vitreous body V. Thus, the vitreous body V is a region having a higher luminance value between a plurality of regions defined by the outer edge (boundary) of the vitreous body in a region on the vitreous body side of a region regarding the retina, and the surface layer of the retina in a tomographic image. Based on the above, the detection unit 332 can detect the vitreous body V based on the luminance value of the tomographic image. At this time, after the boundary lines are detected, the retinal region is specified, and a region above the retinal region is obtained as the vitreous body V. However, the order of obtaining the vitreous body V is not limited to this. Alternatively, the retinal region may be specified first, and then, the boundary lines of regions above the retinal region may be tracked, thereby obtaining the vitreous boundary.

<Step S256: Detachment Detection>

In step S256, the detection unit 332 detects a detachment region (posterior vitreous pocket) of the vitreous body. A detachment region S of the vitreous body is a shaded region defined by the vitreous body V and the boundary line L1 illustrated in FIG. 5C. More specifically, the detachment region S of the vitreous body is a region having a lower luminance value between a plurality of regions defined by the outer edge (the boundary) of the vitreous body in a region further on the vitreous body side than a region regarding the retina, and the surface layer of the retina in a tomographic image. In a case where vitreous detachment is not caused, the detachment region S is not detected.

<Step S206: Quantification>

In step S206, the calculation unit 333 quantifies the vitreous region. As the quantification of the vitreous region, the calculation unit 333 quantifies the detachment region S of the vitreous body. As the quantification, the calculation unit 333 obtains the thickness, the width, the area, and the volume of the detachment region S. The thickness of the detachment region S can be calculated by obtaining the difference in z-coordinate between the vitreous boundary line and the retinal boundary line at each coordinate point on an xz plane to obtain the number of pixels, and multiplying the number of pixels in the z-direction by the pixel resolution [μm] in the z-direction. The width of the detachment region S can be calculated by obtaining the difference between the smallest x-coordinate and the largest x-coordinate of the detachment region S to obtain the number of pixels, and multiplying the number of pixels in the x-direction by the pixel resolution [μm] in the x-direction. The area and the volume can be calculated similarly to such calculation. Further, in a case where the volume of the detachment region S is obtained, a calculation method differs depending on the scan pattern when the image is captured. In a case where the image is captured by a raster scan, the volume can be calculated by adding, in the y-axis direction, areas obtained in the respective tomographic images. When the image is captured by a radial scan, the volume is calculated by correcting the volume in a circumferential direction. When the volume is captured by a cross scan, the volume is not calculated. Although a description has been given using the detachment region S as an example, the thickness, the width, the area, and the volume of the vitreous body V can also be obtained in a similar manner.

Figure 6A:
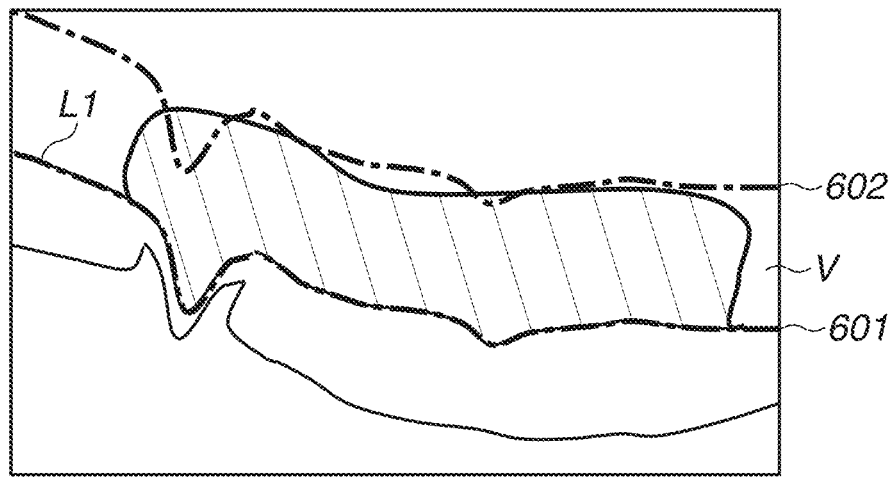
FIGS. 6A and 6B are diagrams illustrating quantified regions in the image processing apparatus.
Figure 6B:
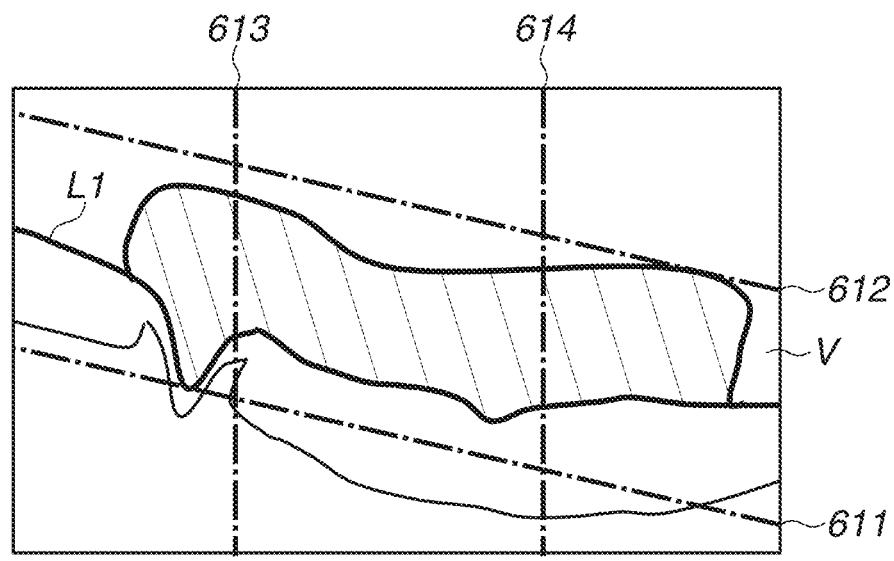

To calculate the thickness, the width, the area, and the volume of the detachment region S or the vitreous body V, the calculation may not be made in the entire range appearing in the tomographic image, but may be made only in a particular region. With reference to FIGS. 6A and 6B, this case is described. FIG. 6A is an example illustrating a quantified region surrounded by a one-dot chain line 601, which is a curved line based on the retinal boundary L1, and a one-dot chain line 602, which is a curved line set in a certain range (e.g., 500 μm) above the one-dot chain line 601. The calculation may be made only in such a region. Further, as in FIG. 6B, the calculation may be made in a region defined by a one-dot chain line 611, which is a straight line based on the retinal boundary L1, a one-dot chain line 612, which is a straight line, and one-dot chain lines 613 and 614, which are straight lines set in the vertical direction. As illustrated in FIGS. 6A and 6B, a region where values are calculated may be a region defined by curved lines and straight lines. A defined region may be set in both the vertical direction and the horizontal direction as illustrated in FIG. 6B, or may be set in either one of the vertical direction and the horizontal direction as in FIG. 6A. Further, this region may be automatically specified by the specifying unit 334, or may be specified based on a position input through the input unit 700. As an input method, in a case where the input unit 700 is a mouse or a touch operation screen, any of the one-dot chain lines 601 to 614 may be moved by a drag and specified. Alternatively, in a case where the input unit 700 is a keyboard, numerical values may be input to specify the positions of the one-dot chain lines 601 to 614. A place can be specified not only by horizontal and vertical movements but also by the angle of rotation.

<Step S207: Display>

Figure 7:
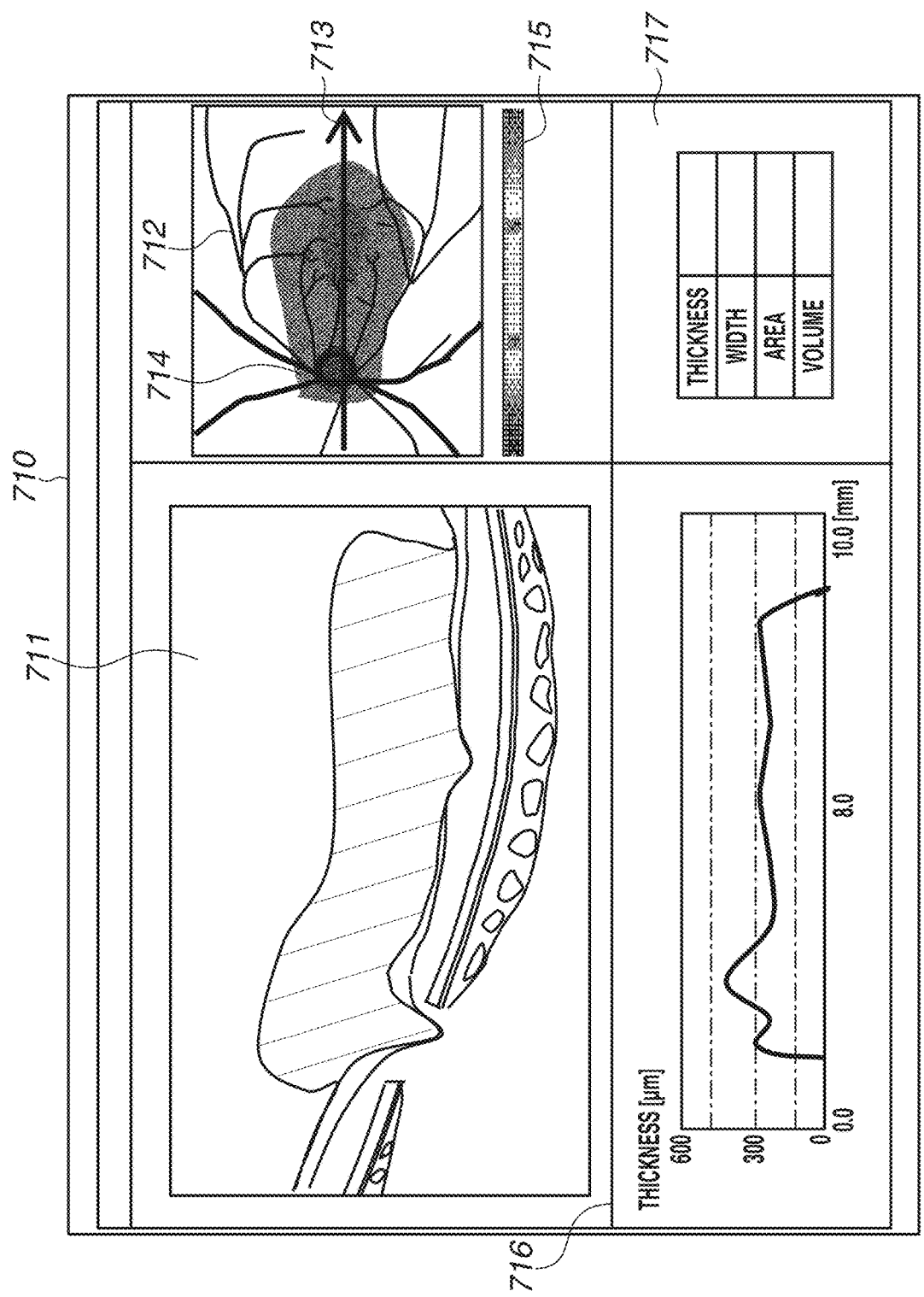
FIG. 7 is an example of a display screen of a display unit of the image processing system.

In step S207, the display control unit 305 causes the display unit 600 to display an analysis result. FIG. 7 illustrates an example of a screen for displaying on the display unit 600 the result of analyzing a vitreous detachment region on data three-dimensionally acquired by a raster scan in the present exemplary embodiment. FIG. 7 illustrates a tomographic image observation screen 710, a tomographic image 711, a fundus image 712, an image capturing position 713 with a scan pattern mark of the image capturing, a vitreous detachment region 714, which is displayed on the fundus image 712 in a superimposed manner, a color bar 715, which indicates which color corresponds to what micrometers in a case where the thickness of the vitreous detachment region 714 is displayed in color, a thickness graph 716 of the vitreous detachment region 714, and an indicator 717, which quantifies the vitreous detachment region 714. If captured by a raster scan, the tomographic image 711 is three-dimensional data including at least three or more tomographic images. Thus, the tomographic image 711 can be displayed by switching the tomographic image 711 to a tomographic image obtained by capturing another position. The thickness, the width, and the area of the vitreous detachment region 714 in the thickness graph 716 and the indicator 717 are numerical values obtained from a single tomographic image. Thus, in a case where the tomographic image 711 displayed on the tomographic image observation screen 710 is displayed by switching the tomographic image 711, it is desirable that the graph 716 and the indicator 717 should also display corresponding numerical values in conjunction with the switching of the tomographic image 711. In the indicator 717, however, in a case where representative values such as a maximum value, a minimum value, an average value, and a median of all the tomographic images are displayed, it is not necessary to change the numerical values in conjunction with the switching of the tomographic image 711. Further, the thickness of the detachment region is defined by the distance between the retinal layer boundary and the detachment region. Alternatively, a feature part of the retina such as a macular portion may be detected from the retina, and the distance from the feature part may be displayed.

Although not illustrated here, each of the quantified regions illustrated in FIGS. 6A and 6B is displayed on the tomographic image 711 in a superimposed manner so that the place and the size of the quantified region can be set on the tomographic image observation screen 710. The display and hiding of the quantified region can be switched.

In the present exemplary embodiment, a description has been given of the detection and the quantification of a detachment region and the specifying of a quantified region. The present invention, however, is not limited to this. For example, the vitreous boundary line detected by the detection unit 332 may only be displayed on the tomographic image 711 in a superimposed manner. The display of the vitreous boundary line can even out variation in determinations depending on individuals.

<Step S208: Determination of Whether to End Processing>

In step S208, an instruction acquisition unit (not illustrated) externally acquires an instruction indicating whether to end the capturing of tomographic images performed by the image processing system 100. This instruction is input by the operator, using the input unit 700. If the image processing system 100 acquires an instruction to end the processing (YES in step S208), the processing ends. If, on the other hand, the capturing of images is to be continued without ending the processing (NO in step S208), the processing returns to step S202. In step S202, the capturing of images is continued. With the above operations, the processing of the image processing system 100 is performed.

According to the above-described configuration, it is possible to detect the whole structure of the vitreous body using a tomographic image captured by OCT and quantitatively obtain the vitreous structure. Consequently, it is possible to quantitatively obtain a vitreous structure, which has been subjectively determined.

In the first exemplary embodiment, the whole structure of the vitreous body is detected, thereby quantitatively obtaining the vitreous structure. A second exemplary embodiment is characterized in detecting and quantifying a fibrous structure (or a linear structure or a folded structure) within the vitreous body. Components having functions similar to those in the first exemplary embodiment are not described here. The present exemplary embodiment is different from the first exemplary embodiment in a second detection unit 832 and a second calculation unit 833 of an image processing unit 803. The processing flow in the present exemplary embodiment is different from that in the first exemplary embodiment in detection in step S905, quantification in step S906, and display in step S907 in FIG. 9A. With reference to FIGS. 8 to 13, the processing of the present exemplary embodiment is described below.

Figure 8:
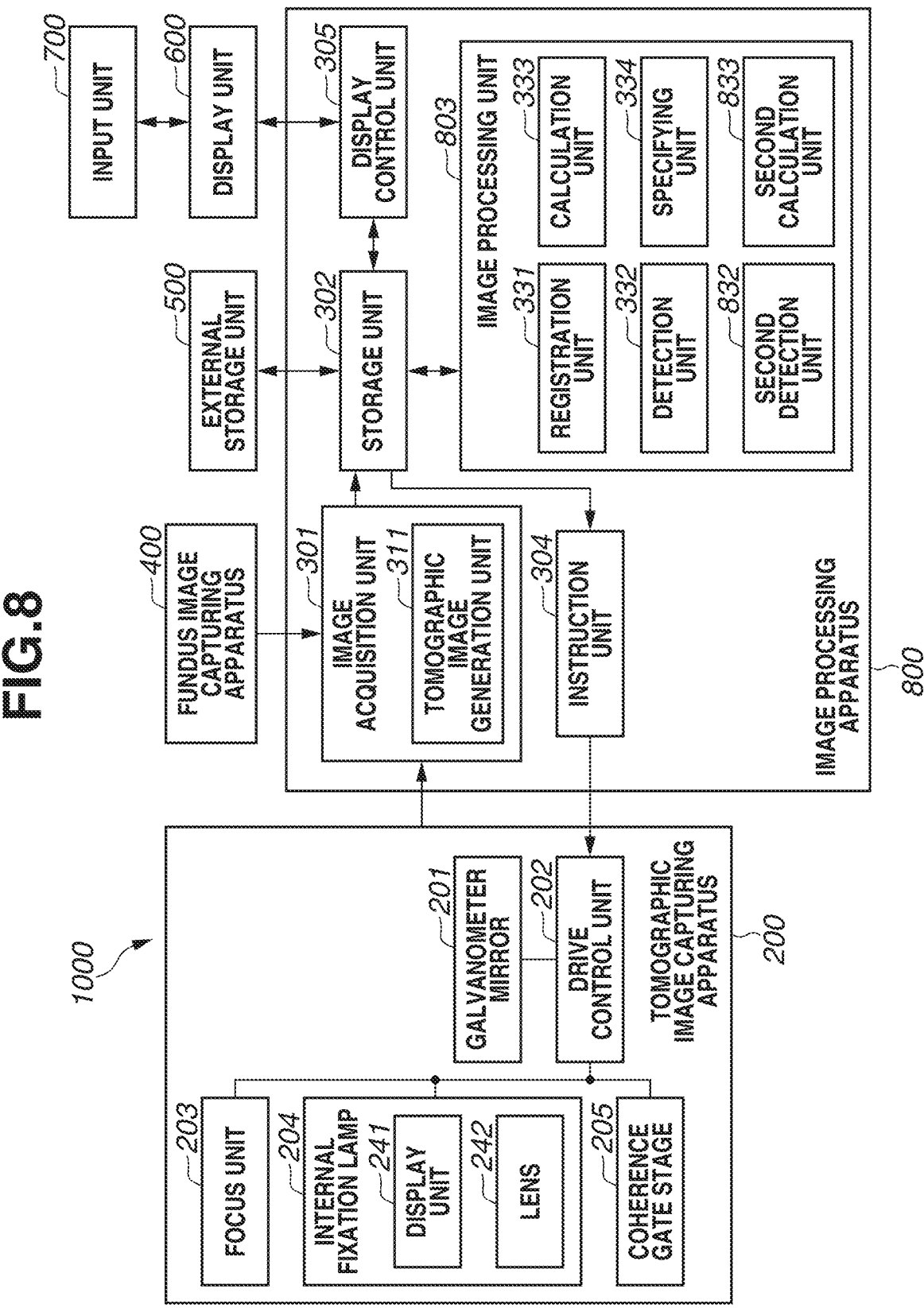
FIG. 8 is a block diagram illustrating a configuration of an image processing system.
Figure 9A:
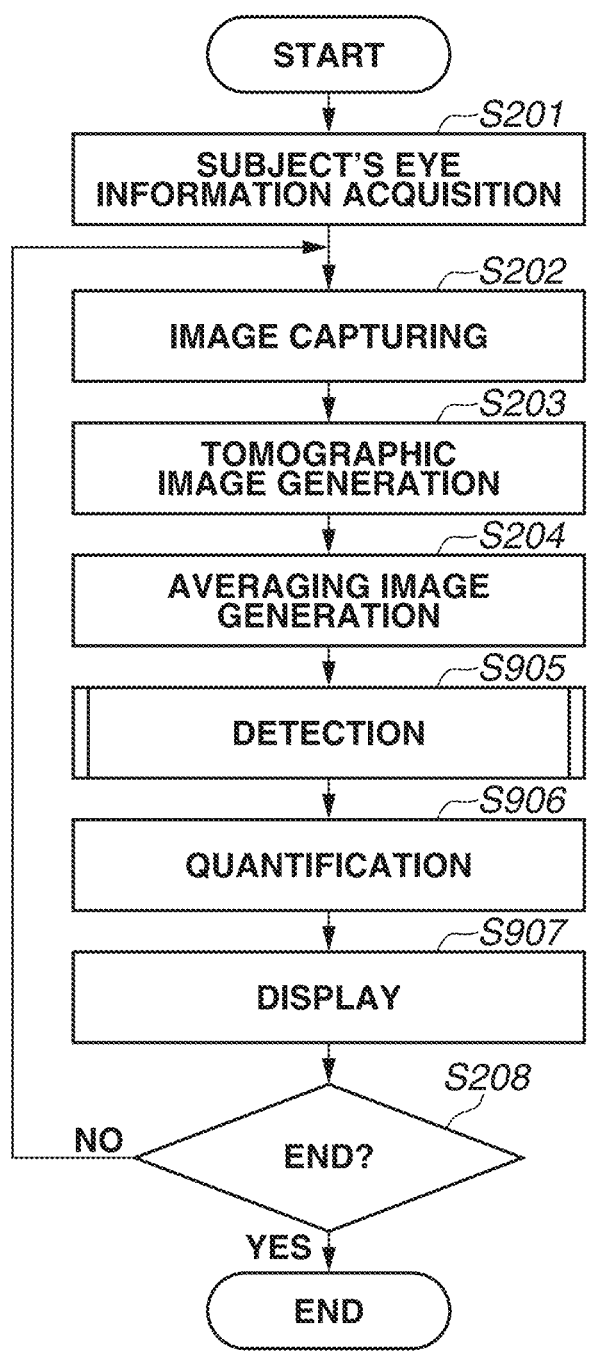
FIGS. 9A and 9B are flowcharts illustrating a flow of processing of the image processing system.
Figure 9B:
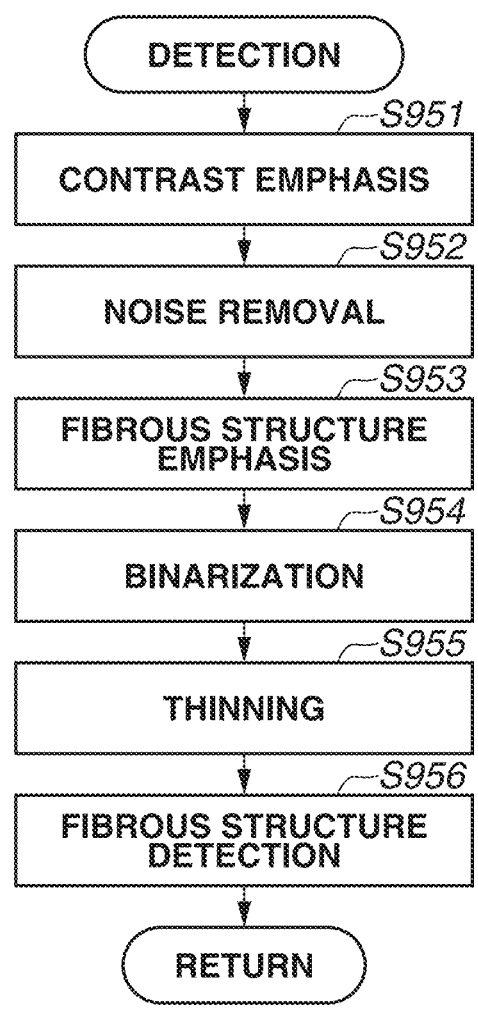

FIG. 8 is a block diagram illustrating the configuration of an image processing apparatus 800 according to the present exemplary embodiment. The image processing apparatus 800 according to the present exemplary embodiment is different from the image processing apparatus 300 according to the first exemplary embodiment in that the image processing apparatus 800 includes a second detection unit 832 and a second calculation unit 833. The second detection unit 832 detects a fibrous structure within the vitreous body. The second calculation unit 833 quantifies the fibrous structure. Next, with reference to FIGS. 9A and 9B, the processing flow in the present exemplary embodiment is described. FIG. 9A is a flowchart illustrating a flow of the operation processing of the whole system according to the present exemplary embodiment. A description is given of steps S905 to S907, which are processes different from the first exemplary embodiment. The other steps are similar to those in the first exemplary embodiment.

<Step S905: Detection>

In step S905, the second detection unit 832 detects a fibrous structure within the vitreous body. With reference to a flowchart in FIG. 9B and FIGS. 10A, 10B, and 11, the processing of the second detection unit 832 is described.

<Step S951: Contrast Emphasis>

In step S951, the second detection unit 832 emphasizes the contrast of the tomographic image generated in steps S203 and S204. This process is similar to the process of step S251.

<Step S952: Noise Removal>

In step S952, the second detection unit 832 removes noise from the tomographic image of which the low luminance region is subjected to the contrast emphasis. This process is similar to the process of step S252. Similar to the first exemplary embodiment, the order of the processes of steps S951 and S952 may be reversed.

<Step S953: Fibrous Structure Emphasis>

In step S953, the second detection unit 832 performs a fibrous structure emphasis process. As the fibrous structure emphasis process, for example, a fibrous structure emphasis filter based on the eigenvalues of the Hessian matrix is used. Using this filter, it is possible to emphasize the second-order local structure of three-dimensional luminance distribution based on the relationships between three eigenvalues ($\lambda_1, \lambda_2, \lambda_3$) of the Hessian matrix. The Hessian matrix is given by the expression (3). The Hessian matrix is a square matrix created by all second-order partial derivatives of a multi-variable function. I represents the luminance value of the image. Expression 3 illustrates the relationships between the eigenvalues of the Hessian matrix. The expression (4) illustrates a conditional expression of the eigenvalues for emphasizing the fibrous structure.

$$H = \begin{pmatrix} I_{xx} & I_{xy} & I_{xz} \\ I_{yx} & I_{yy} & I_{yz} \\ I_{zx} & I_{zy} & I_{zz} \end{pmatrix} \quad (3)$$

$$\lambda_3 \leq \lambda_2 \leq \lambda_1 \qquad (4)$$

$$\lambda_3 \ll \lambda_2 = \lambda_1 = 0$$

From the three eigenvalues obtained by these expressions, the following expression (5) is obtained, whereby it is possible to emphasize the fibrous structure of the vitreous body. In expression 5, $\omega(\lambda_s; \lambda_t)$ is a weight function and is illustrated by expression (6). In expression 6, $\gamma$ and $\alpha$ are weights.

$$S_{sheet}\{f\} = \begin{cases} |\lambda_3| \cdot \omega(\lambda_2; \lambda_3) \cdot \omega(\lambda_1; \lambda 3) & \lambda_3 < 0 \\ 0 & \text{otherwise} \end{cases} \qquad (5)$$

$$\omega(\lambda_s; \lambda_t) = \begin{cases} \left(1 + \frac{\lambda_s}{|\lambda_t|}\right)^y & \lambda_t \leq \lambda_s \leq 0 \\ \left(1 - \alpha \frac{\lambda_s}{\lambda_t}\right)^y & \frac{|\lambda_t|}{\alpha} > \lambda_s > \\ 0 & \text{otherwise} \end{cases} \qquad (6)$$

The fibrous structure emphasis filter based on the eigenvalues of the Hessian matrix is an example of a case where the fibrous structure emphasis filter processes data captured by a three-dimensional raster scan. Alternatively, the fibrous structure emphasis filter may process each of two-dimensional tomographic images. In this case, two eigenvalues of the Hessian matrix are obtained, and a linear structure is detected.

The fibrous structure emphasis filter is not limited to a filter based on the eigenvalues of the Hessian matrix. Alternatively, for example, as a filter for emphasizing a linear structure in two-dimensional tomographic images, a difference filter such as a Sobel filter or a Laplacian filter may be used. Yet alternatively, a line segment emphasis filter based on contrast for, when a line segment is a structural element, calculating the difference between an average value of an image density value in the structural element and an average value of a local region surrounding the structural element may be used. Yet alternatively, top-hat calculation for simply using a line segment as a structural element may be used. Yet alternatively, a band-pass filter for filtering a particular frequency domain as frequency filtering may be used.

<Step S954: Binarization>

In step S954, the second detection unit 832 performs binarization. As a method for the binarization, in a case where the range of the luminance value of the fibrous structure of the vitreous body after the fibrous structure emphasis is known from the apparatus characteristics, a fixed threshold may be used. Alternatively, a threshold may be dynamically determined by a percentile method or a discrimination analysis method. As the setting of the threshold, a single threshold may not be set for the whole image, but local regions (rectangular or circular regions) may be set, and a threshold may be set using an average value or a median with respect to each local region.

Figure 10A:
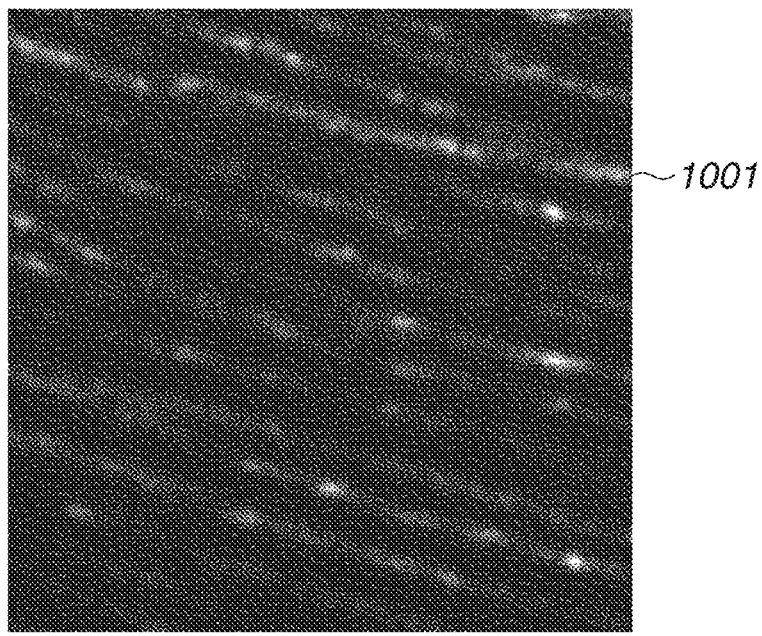
FIGS. 10A and 10B are diagrams illustrating processing of an image processing apparatus.
Figure 10B:
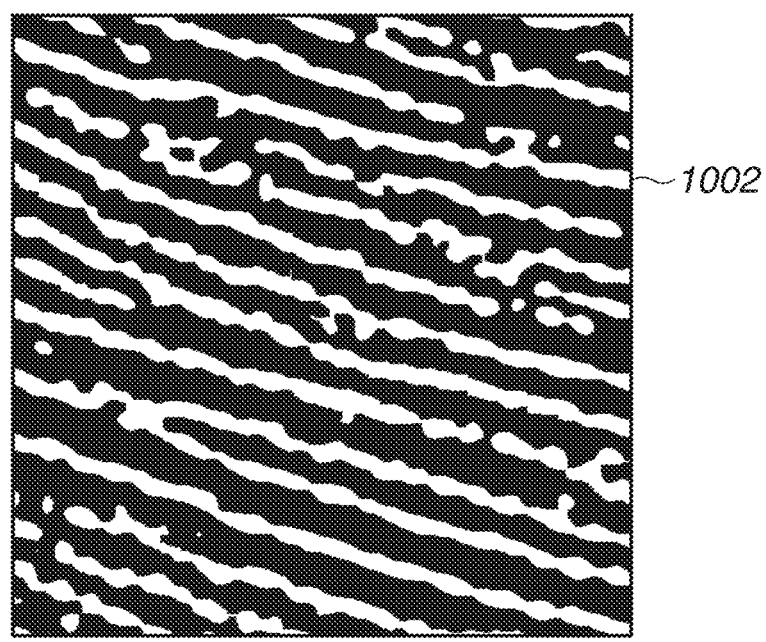

FIGS. 10A and 10B illustrate examples of the fibrous structure of the vitreous body and a binarized image. FIG. 10A is a diagram illustrating the fibrous structure of the vitreous body. In FIG. 10A, a white linear region 1001 indicates the fibrous structure. FIG. 10B is an image binarized after the fibrous structure is emphasized by performing the processes of steps S951 to S954. FIG. 10B illustrates a region 1002, which is obtained by binarizing the white linear region 1001 in FIG. 10A. As illustrated in FIG. 10B, a fibrous structure (linear structure) is detected from the vitreous body V. The morphological process illustrated in step S254 may be applied to the image after the binarization, thereby executing the process of connecting the discontinuity of lines or removing noise.

<Step S955: Thinning>

Figure 11:
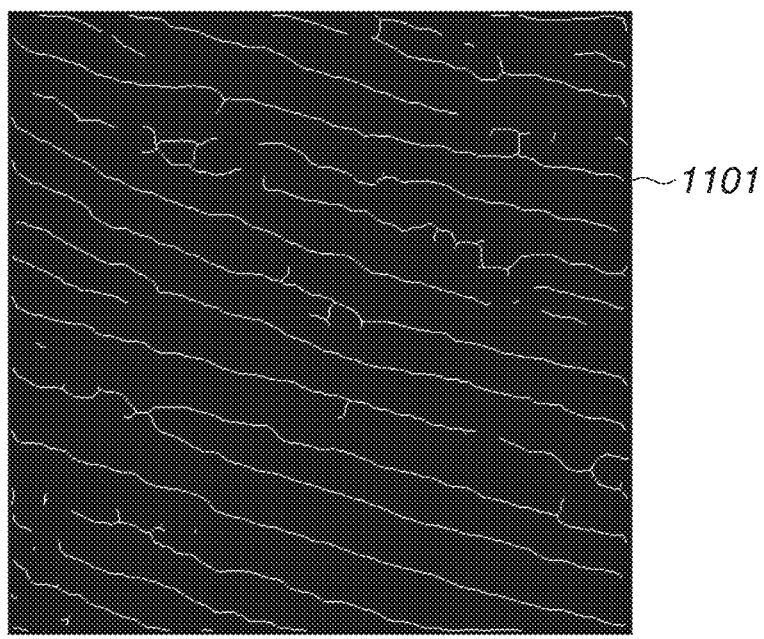
FIG. 11 is a diagram illustrating the processing of the image processing apparatus.

In step S955, the second detection unit 832 performs thinning. In the thinning, the second detection unit 832 performs the process of extracting a center line of a width of one pixel while maintaining the connectivity of a figure. As a method for the thinning, a Hilditch method or a Tamura method is used. FIG. 11 illustrates an example of an image after the fibrous structure of the vitreous body is thinned. FIG. 11 illustrates a region 1101, which is obtained by thinning the fibrous structure 1002 in the binarized image in FIG. 10B.

<Step S956: Fibrous Structure Detection>

In step S956, the second detection unit 832 detects the fibrous structure. In the detection of the fibrous structure, data regarding the fibrous structure obtained up to step S955 is saved as a mask image in which is a background and 255 is a fiber. Alternatively, a labeling process is performed to label each fiber of the fibrous structure 1101. By the labeling process, the same label is assigned to joined fibers, and different labels are assigned to different connection components. The fibrous structure obtained in steps S951 to S956 may not be detected in the whole tomographic image, but as illustrated in the first exemplary embodiment, the region of the vitreous body V may be detected, and the above process may be performed only on this region.

<Step S906: Quantification>

In step S906, the second calculation unit 833 quantifies the fibrous structure of the vitreous body. As the quantification, the number of fibers of the fibrous structure, the occupancy of the fibrous structure, and the fiber density are obtained. In a case where the number of fibers is obtained, it is possible, due to the labeling process in step S956, to obtain how many fibers are present. At this time, a short fiber (e.g., a line over several pixels) can be noise, and therefore is excluded from the count of the number of fibers.

Figure 12A:
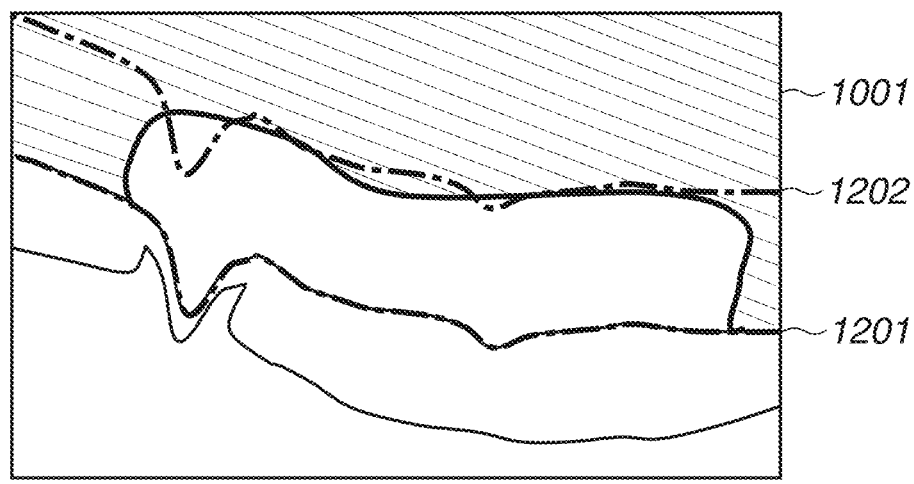
FIGS. 12A and 12B are diagrams illustrating quantified regions in the image processing apparatus.
Figure 12B:
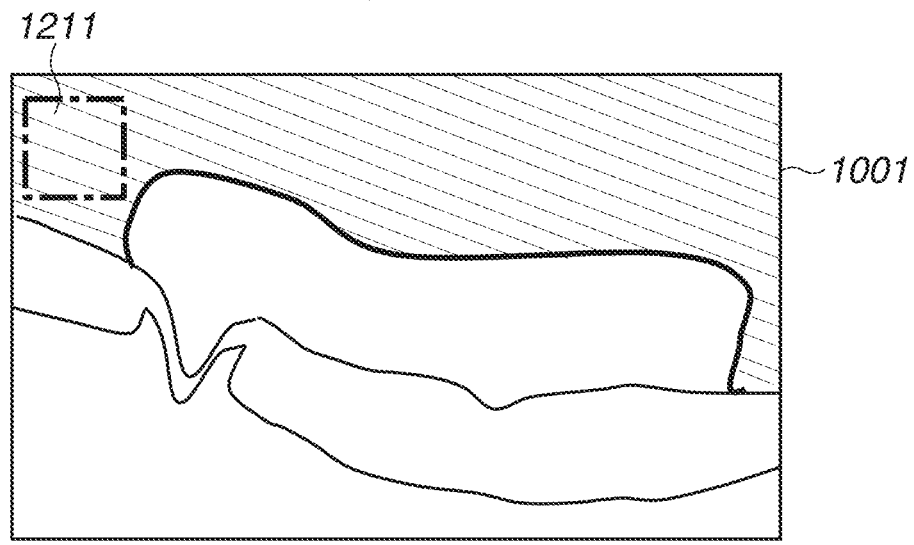

To calculate the occupancy and the fiber density, numerical values are calculated by specifying a particular region. With reference to FIGS. 12A and 12B, this case is described. FIG. 12A is an example illustrating a quantified region surrounded by a one-dot chain line 1201, which is a curved line based on the retinal boundary L1, and a one-dot chain line 1202, which is a curved line set in a certain range (e.g., 500 μm) above the one-dot chain line 1201. FIG. 12B is an example where a one-dot chain line region 1211 of a certain size is set in the region of the vitreous body V. Further, this region may be automatically specified by the specifying unit 334, or may be specified based on a position input through the input unit 700. As an input method, in a case where the input unit 700 is a mouse or a touch operation screen, any of the one-dot chain lines 1201 to 1211 may be moved by a drag to specify a region. Alternatively, in a case where the input unit 700 is a keyboard, numerical values may be input to specify the positions of the one-dot chain lines 1201 to 1211. A place can be specified not only by horizontal and vertical movements but also by the angle of rotation.

The occupancy is the proportion of an object to a region, and the unit of the occupancy is defined by %. In the present exemplary embodiment, the occupancy is the proportion of the fibrous structure 1001 present in the region 1211. The presence of the fibrous structure is determined by, for example, the fibers 1101 after the thinning. Further, the fiber density is the number of fibers in a unit distance, and the unit of the fiber density is defined by fibers/mm. In this case, the fiber density is defined by the number of fibers present on a single line in the depth direction (Z-direction) or the normal direction to retinal layers. Alternatively, in a case where the fiber density is defined by an area, the fiber density is the number of fibers in a unit area, and the unit of the fiber density is defined by fibers/mm$^2$. In the case of three-dimensional data, the fiber density is the number of fibers in a unit volume, and the unit of the fiber density is defined by fibers/mm$^3$. In the present exemplary embodiment, the fiber density is the number of fibers 1001 present in the region 1211. In the above definitions, a region of 1 mm×1 mm is used. However, in a case where the region 1211 cannot secure this size, the units may be changed.

<Step S907: Display>

In step S907, the display control unit 305 causes the display unit 600 to display an analysis result. FIG. 13 illustrates an example of a screen for displaying on the display unit 600 the result of analyzing a fibrous structure region of the vitreous body on data three-dimensionally acquired by a raster scan in the present exemplary embodiment. FIG. 13 illustrates a tomographic image observation screen 710, a tomographic image 1311, a fundus image 1312, an image capturing position 713 with a scan pattern mark of the image capturing, a color map 1314, which displays the number of fibers of the fibrous structure on the fundus image 1312 in a superimposed manner, and a color bar 1315, which indicates which color corresponds to how many fibers in the number of fibers of the fibrous structures in the color map 1314, a number graph 1316, which indicates the number of fibers of the fibrous structure, and an indicator 717, which quantifies the fibrous structure region.

Similar to the first exemplary embodiment, in the case of data including a plurality of tomographic images, the tomographic image 1311 can be displayed by switching the tomographic image 1311. According to this switching, in a case where the tomographic image 1311 is displayed by switching the tomographic image 1311, it is desirable that the number graph 1316 and the indicator 1317 should also display corresponding numerical values in conjunction with the switching of the tomographic image 1311. In the indicator 1317, however, in a case where the number of fibers, the occupancy, and the fiber density are obtained from the whole data, it is not necessary to change the numerical values in conjunction with the switching of the tomographic image 1311. It is desirable to perform display so that each of the values can be understood whether it is a numerical value calculated from a single tomographic image, or a total value calculated from a plurality of tomographic images.

The color map 1314 may display data obtained by quantifying the occupancy and the fiber density in color. Further, colors may be displayed in a superimposed manner not only on the map but also on the tomographic image.

According to the above-described configuration, it is possible to detect a fibrous structure within the vitreous body using a tomographic image captured by OCT and quantitatively obtain the fibrous structure within the vitreous body. Consequently, it is possible to quantitatively obtain a fibrous structure within the vitreous body, which has been subjectively determined.

In the first and second exemplary embodiments, the whole structure of the vitreous body and a fibrous structure within the vitreous body are detected and quantitatively obtained. A third exemplary embodiment is characterized in performing comparison display of these quantification results. Components having functions similar to those in the first and second exemplary embodiments are not described here. The present exemplary embodiment is different from the first and second exemplary embodiments in a selection unit 1431 and a difference detection unit 1432 in an image processing unit 1403. The processing flow in the present exemplary embodiment is different from those in the first and second exemplary embodiments in detection performed in step S1505 to step S1509 in FIG. 15A. With reference to FIGS. 14 to 17, the processing of the present exemplary embodiment is described below.

Figure 14:
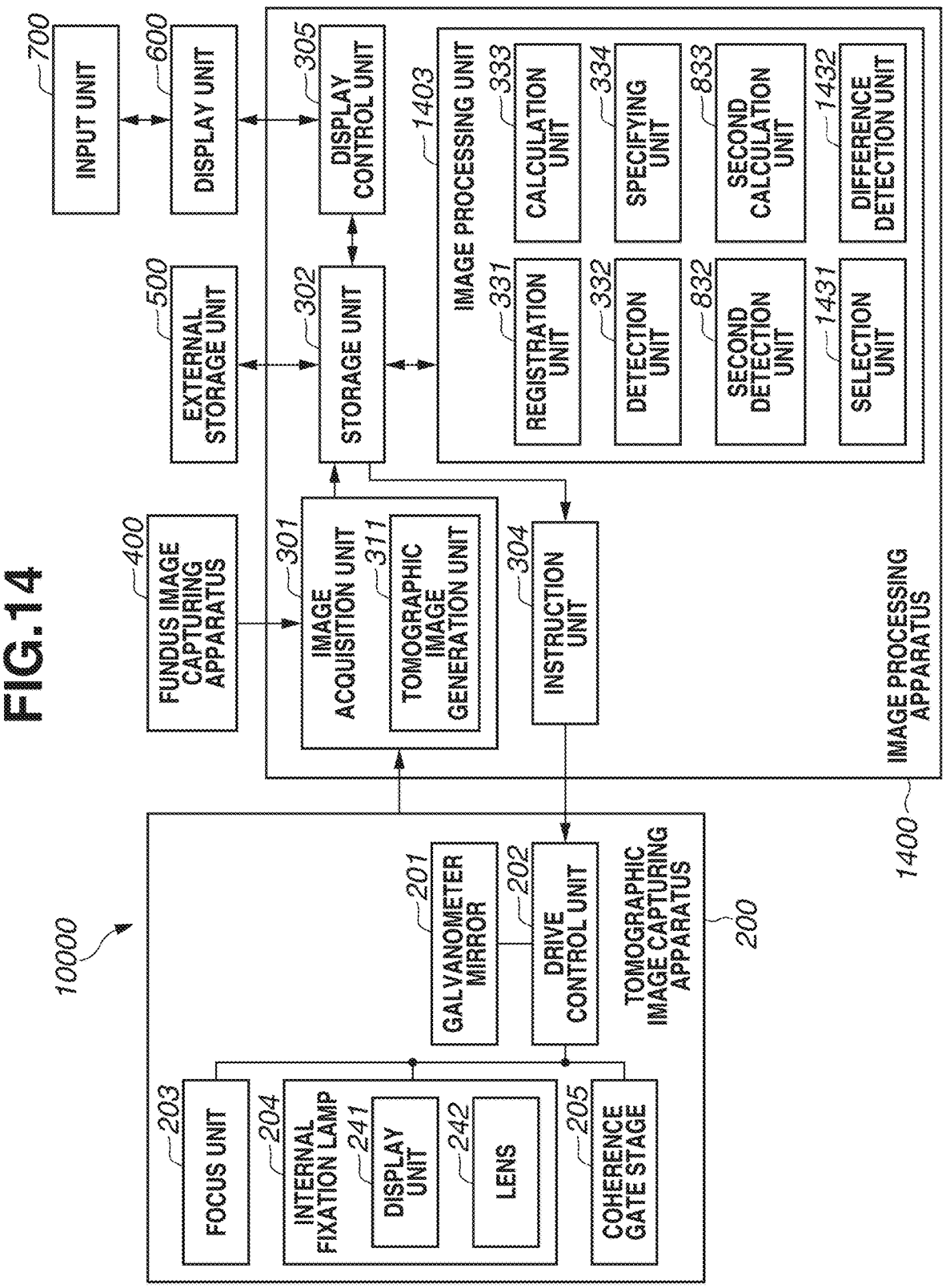
FIG. 14 is a block diagram illustrating a configuration of an image processing system.

First, FIG. 14 is a block diagram illustrating a configuration of an image processing apparatus 1400 according to the present exemplary embodiment. The image processing apparatus 1400 according to the present exemplary embodiment is different from the image processing apparatuses 300 and 800 according to the first and second exemplary embodiments in that the image processing apparatus 1400 includes a selection unit 1431 and a difference detection unit 1432. The selection unit 1431 selects pieces of image data to be compared. The difference detection unit 1432 detects the difference between the pieces of compared data. Next, with reference to FIGS. 15A and 15B, the processing flow in the present exemplary embodiment is described. FIG. 15A is a flowchart illustrating the flow of operation processing of the whole system according to the present exemplary embodiment. FIG. 15B is a flowchart illustrating a flow of processing regarding comparison display.

<Step S1505: Detection>

In step S1505, as illustrated in the first and second exemplary embodiments, the whole structure of the vitreous body and a fibrous structure within the vitreous body are detected.

<Step S1506: Quantification>

In step S1506, the whole structure of the vitreous body and the fibrous structure within the vitreous body are quantified. In the present exemplary embodiment, a case is described where the detachment of the vitreous structure is quantified and subjected to comparison display.

<Step S1507: Determination of Whether to Execute Comparison Display>

In step S1507, if the operator selects a user interface for selecting comparison display (not illustrated) (YES in step S1507), the processing proceeds to step S1508. If the user interface for selecting comparison display is not selected (NO in step S1507), the processing proceeds to step S1509. Display in step S1509 is similar to the display illustrated in the first and second exemplary embodiments, and therefore is not described in the present exemplary embodiment.

<Step S1508: Comparison Display>

In step S1508, comparison display is performed. Examples of the comparison display include selection comparison between any pieces of selected data, comparison between pieces of time-series data captured at different times in the same subject's eye (follow-up), left/right eye comparison for comparing the left and right eyes of the same subject, and database comparison for comparing data with a standard database. The standard database is data having statistical values created from data of many eyes and is created by integrating data according to race and age. In the field of ophthalmology, the standard database may be classified by parameters specific to eyes, such left and right eyes or eye axial length. The standard database is set in such a manner that the range of 95% of normal data is a normal range, the range of 4% of the normal data is a borderline range, and the range of the remaining 1% of the normal data is an abnormal range. With reference to the flow in FIG. 15B, these types of comparison display are described.

<Step S1581: Reference Data Acquisition>

In step S1581, reference data for performing a follow-up is acquired. The reference data for a follow-up is, for example, data subjected to the quantification up to step S1506 and selected when the user interface for selecting comparison display is selected in step S1507.

<Step S1582: Comparison Data Selection>

In step S1582, the selection unit 1431 selects data that can be compared with the reference image. In the selection of data in selection comparison or a follow-up, data of the same patient, the same eye, the same scan mode, and the same image capturing range can be selected. For example, in a case where data selected as the reference image is data obtained by capturing the right eye of a patient having a patient ID "00001" by a raster scan in the range of 10 mm, the selection unit 1431 selects data satisfying these conditions. Then, the selection unit 1431 displays on the display unit 600 a data list of data that can be compared. The operator selects any data from the displayed data list. Further, in the case of left/right eye comparison, data of a different eye from that of the reference image, the same patient, the same scan mode, and the same image capturing range can be selected. Then, the selection unit 1431 displays on the display unit 600 a data list of data that can be compared. Further, in the case of database comparison, a database created based on the same patient, the same eye, the same scan mode, and the same image capturing range is selected. In the database comparison, data that meets the reference is automatically selected without displaying a database list to the operator.

An example has been illustrated where, after the selection unit 1431 selects data, the operator finally selects a display image. The present invention, however, is not limited to this. For example, a follow-up is intended to compare a plurality of pieces of time-series data, and therefore, the selection unit 1431 may select and display all pieces of data that meet the conditions of the reference image. Alternatively, the selection unit 1431 may display data by selecting a determined period (e.g., over the past three years), the determined number of times (e.g., in the last five times), or discrete data (e.g., on an annual basis).

<Step S1583: Difference Data Creation>

In step S1583, the difference detection unit 1432 detects the difference between the reference image selected in step S1581 and the comparison image selected in step S1582. In the case of selection comparison or a follow-up, the difference detection unit 1432 performs registration between the reference image and the comparison image to detect the difference between the reference image and the comparison image. For the registration, a fundus image captured by the fundus image capturing apparatus 400 is used. As a method for the registration, positions can be adjusted based on the degree of similarity between the images, or the registration can be performed using a feature point by detecting the feature point such as blood vessels from the images. In a case where the tomographic image is captured by a raster scan, the tomographic image can also be used as an image for the registration. In a case where the tomographic image is used, the A-scans in the tomographic image are subjected to addition averaging in the Z-axis direction (depth direction), thereby generating a simulated fundus image. Then, the registration is performed using the simulated fundus image. After the registration between the reference image and the comparison image is performed, the difference between pieces of data that is to be viewed is detected.

Figure 16A:
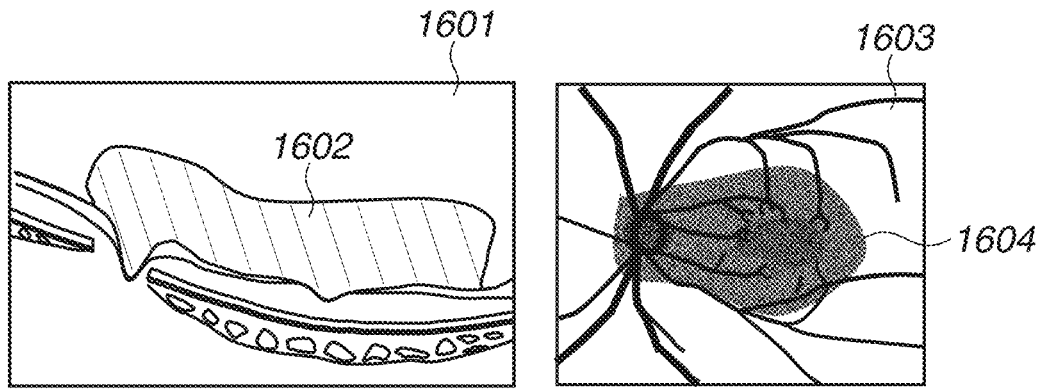
FIGS. 16A, 16B, and 16C are diagrams illustrating processing of an image processing apparatus.
Figure 16B:
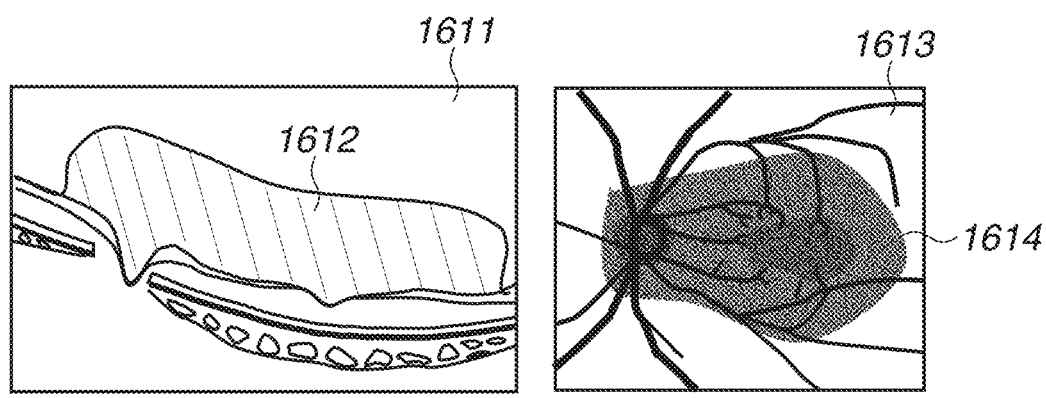
Figure 16C:
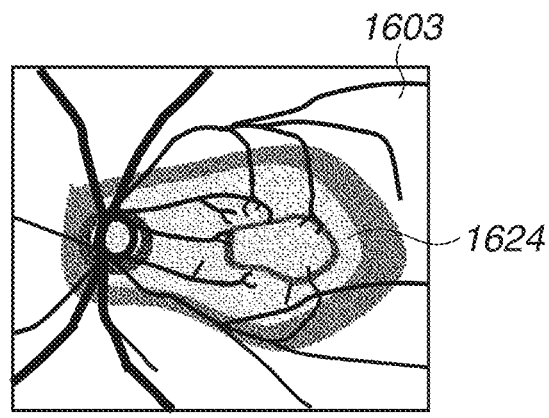

In the present exemplary embodiment, with reference to FIGS. 16A to 16C, a case is described where vitreous detachment is compared in data three-dimensionally acquired by a raster scan. FIG. 16A illustrates a tomographic image 1601 as a reference image, a vitreous detachment region 1602, a fundus image 1603, and a vitreous detachment map 1604, which displays the vitreous detachment on the fundus image 1603 in a superimposed manner and displays the thickness of the vitreous detachment region 1602 in color. FIG. 16B illustrates a tomographic image 1611 as a comparison image, a vitreous detachment region 1612, a fundus image 1613, and a vitreous detachment map 1614. FIG. 16C illustrates a difference map 1624, which indicates the difference in vitreous detachment between the reference image and the comparison image. The difference map 1624 is displayed on the fundus image 1603 as a reference in a superimposed manner. In the difference map 1624, a portion of the image having a high density value represents a great difference, and a portion of the image having a low density value represents a small difference. In FIGS. 16A to 16C, an example is illustrated where the detachment region expands in the comparison image. It is desirable that the difference map 1624 should display each region by color-coding the region so that the operator can visually determine the expansion or contraction of the region. For example, in a case where the region expands, the region is displayed in a red-based color. In a case where the region contracts, the region is displayed in a blue-based color.

In the case of left/right eye comparison, the fundus image of the comparison image may be inverted with respect to the reference image to perform registration, thereby detecting the difference, or the difference process itself may be skipped. In a case where the difference process is skipped, comparison display without a difference value is performed in display described below. In the case of database comparison, the reference image is compared with a statistical data in a database, thereby detecting the difference. In the case of database comparison, images are not compared, and maps are compared.

<Step S1584: Display>

Figure 17:
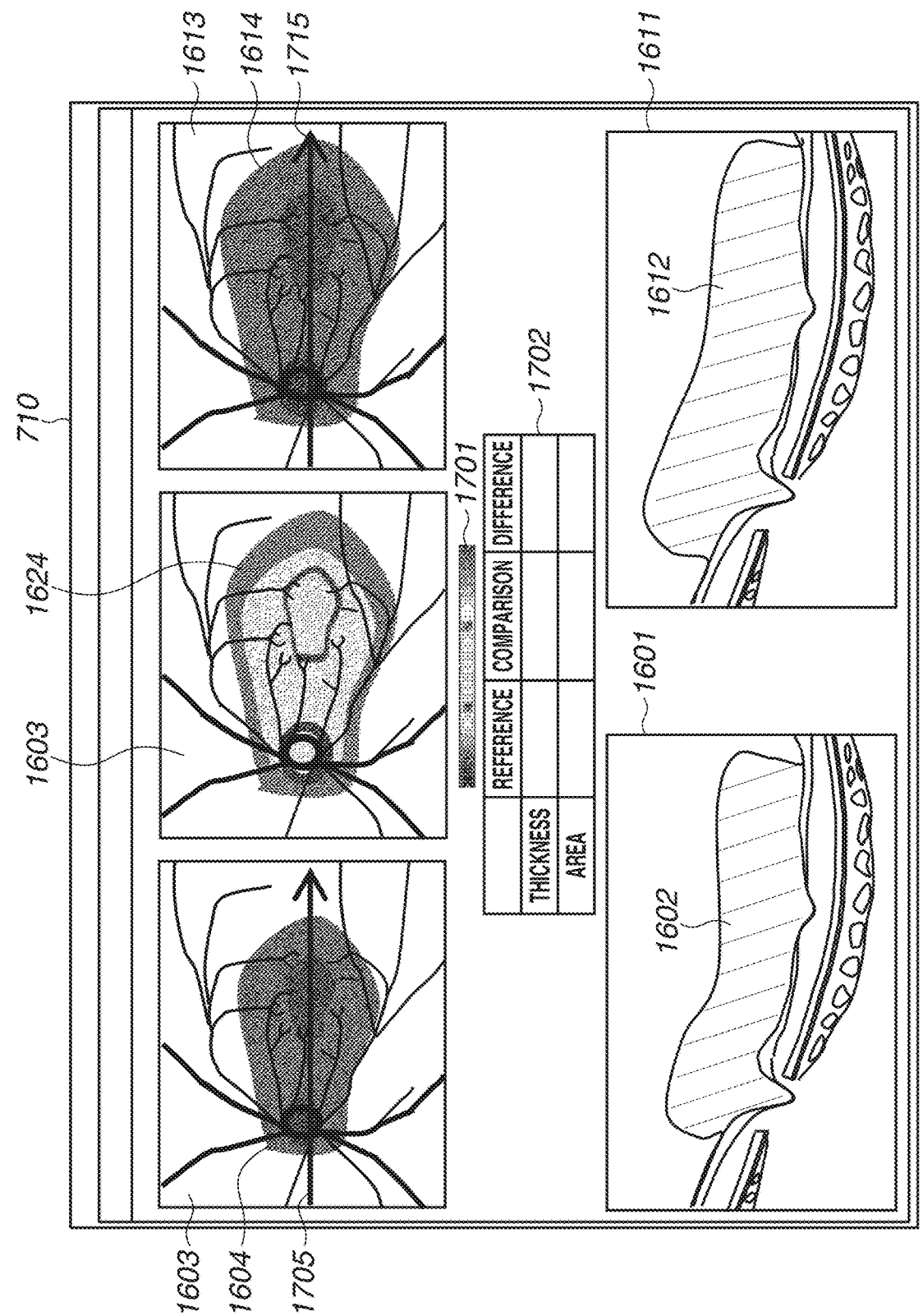
FIG. 17 is an example of a display screen of a display unit of the image processing system.

In step S1584, the display control unit 305 displays a screen for comparison display on the display unit 600. With reference to FIG. 17, this process is described. FIG. 17 illustrates an example of a screen for comparing vitreous detachment in selection comparison. FIG. 17 illustrates a tomographic image observation screen 710, reference images 1601 to 1604, comparison images 1611 to 1614, a difference map 1624, image capturing positions with scan pattern marks 1705 and 1715, a color bar 1701 for the map 1624, and an indicator 1702, which quantifies vitreous detachment regions. The indicator 1702 displays the quantified values of the reference images, the quantified values of the comparison images, and the differences between these quantified values.

Also on the comparison screen, similar to the first and second exemplary embodiments, in the case of data including a plurality of tomographic images, the tomographic images 1601 and 1611 can be displayed by switching the tomographic images 1601 and 1611. In a case where the tomographic images 1601 and 1611 are displayed by switching the tomographic images 1601 and 1611, it is desirable that the indicator 1702 should also display corresponding numerical values in conjunction with the switching of the tomographic images 1601 and 1611. However, in a case where numerical values displayed by the indicator 1702 are representative values of a plurality of pieces of data, it is not necessary to change the numerical values in conjunction with the switching of display of the tomographic images 1601 and 1611.

In a case where the selection unit 1431 automatically selects a plurality of pieces of data for a follow-up in step S1582, images may be able to be displayed by arranging all the image data, or may be able to be displayed by switching the image data. Alternatively, a partial image of the tomographic image or the fundus image may be displayed, and all quantified numerical value data may only be displayed. In a case where a plurality of pieces of numerical value data are displayed, not only the pieces of numerical value data are displayed, but also a graph in which the horizontal axis represents the date and time when the data is acquired and the vertical axis represents the numerical value may be created and displayed.

In the present exemplary embodiment, the processing from image capturing to comparison display is illustrated in a sequential flow, but is not limited to this. For example, display may be performed using data already subjected to image capturing and quantification. In this case, subject's eye information is acquired in step S201, the subsequent processes are skipped, and display is selected in step S1507.

According to the above-described configuration, it is possible to detect the whole structure of the vitreous body and a fibrous structure within the vitreous body using a tomographic image captured by OCT and perform comparison display of the result of quantitatively obtaining the vitreous structure.

<Variations>

In the present exemplary embodiment, an example has been described where contrast emphasis is performed for detecting the vitreous body. Contrast emphasis, however, is not limited to this. Alternatively, contrast emphasis may be performed not for detection but for display. Contrast emphasis for displaying an image may be performed by processing the whole image using the same parameter, or processing each region using a different parameter, or processing a plurality of regions as a single region using a different parameter. A "region" as used herein means a vitreous region, a detachment region of the vitreous body, a retinal region, or a retinal deep layer region. A "vitreous region" refers to a region having a higher luminance value between a plurality of regions defined by the outer edge (boundary) of the vitreous body in a region located on the vitreous body side of a region regarding the retina and the surface layer of the retina in a tomographic image. Further, a "detachment region of the vitreous body" refers to a region having a lower luminance value between a plurality of regions defined by the outer edge (boundary) of the vitreous body in a region located on the vitreous body side of a region regarding the retina and the surface layer of the retina in a tomographic image.

At this time, in a case where each region is processed, the image is displayed by setting a different WW and a different WL for each region. A WW is the range of a luminance value for performing the contrast emphasis, and a WL is a center luminance value of the range where the contrast emphasis is performed. In a case where a plurality of regions is processed as a single region, the image may be displayed by setting a WW and a WL for, for example, a detachment region of the vitreous body, a retinal region, and a retinal deep layer region as a single region, and setting a different WW and a different WL only for a vitreous region. Alternatively, the image may be displayed by setting a WW and a WL for a vitreous region and a vitreous detachment region as a single region, and setting a WW and a WL for a retinal region and a retinal deep layer region as a single region. A WW and a WL are set by creating a frequency histogram of the luminance value in a region to be subjected to the contrast emphasis. Then, the position of a horizontal axis of the top several percent of the histogram and the position of a horizontal axis indicating the maximum frequency of the histogram are detected, whereby it is possible to set the WW and the WL for a portion where the luminance value is to be emphasized.

As described above, the image is displayed by setting a different WW and a different WL with respect to each region or with respect to a plurality of regions, whereby it is possible to display a fibrous structure within a vitreous region having a low luminance value and a layered structure in the retina having a high luminance value in an easily viewable manner in a single image. Further, the process of emphasizing the luminance value of a vitreous region having a lower luminance value than a region regarding the retina, more than the process of emphasizing the luminance value of the region regarding the retina is performed, whereby it is possible to display a fibrous structure within the vitreous region in an easily viewable manner.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)TM), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2016-196895, filed Oct. 5, 2016, and No. 2017-141772, filed Jul. 21, 2017, which are hereby incorporated by reference herein in their entirety.

What is claimed is:

1. An image processing apparatus comprising:
a memory storing a program;
one or more processors, when executing the program, function as:
a first detection unit configured to detect at least one layer of a retina of a subject's eye in a tomographic image of the subject's eye; and
a second detection unit configured to detect, using an intensity information regarding the tomographic image, a boundary between a vitreous body of the subject's eye and a detachment region of the vitreous body in a region, wherein the region is (a) located on a vitreous body side in the tomographic image and (b) identified using information regarding the detected at least one layer.

2. The image processing apparatus according to claim 1, wherein the second detection unit further detects, using the intensity value of the tomographic image, a region defined by the detected boundary and a surface layer of the retina in the detected at least one layer.

3. The image processing apparatus according to claim 2, wherein the processor further functions as:
a calculation unit configured to calculate a value regarding the defined region; and
a display control unit configured to display information regarding the calculated value on a display unit.

4. The image processing apparatus according to claim 3, wherein the value regarding the defined region is a value of at least one of a thickness, a width, an area, and a volume of the defined region.

5. The image processing apparatus according to claim 3, wherein the calculation unit calculates a value regarding a plurality of fibers of linear structure in a region having a higher intensity value between a plurality of regions included in the defined region.

6. The image processing apparatus according to claim 3, wherein the processor further functions as a difference detection unit configured to detect a difference in calculated values using a plurality of tomographic images obtained by capturing the same subject's eye at different times.

7. The image processing apparatus according to claim 3, wherein the processor further functions as a difference detection unit configured to detect a difference in calculated values using a plurality of tomographic images obtained by capturing the left and right eyes of the same subject at different times.

8. The image processing apparatus according to claim 3, wherein the processor further functions as a difference detection unit configured to detect a difference between calculated value and a statistical value regarding the vitreous body.

9. The image processing apparatus according to claim 1, wherein the processor further functions as:
a specifying unit configured to specify, using an intensity information regarding the region regarding the vitreous body of the tomographic image, a plurality of fibers of linear structure in a region regarding the vitreous body, which is a region having a higher intensity value between a plurality of regions defined by the detected boundary and a surface layer of the retina in the detected at least one layer.

10. The image processing apparatus according to claim 9, wherein the processor further functions as a designating unit configured to designate a part of the region on the vitreous body, wherein the specifying unit specifies, using an intensity information regarding the specified part of the region, the plurality of fibers of linear structure in the part of the region designated by the designating unit.

11. The image processing apparatus according to claim 9, wherein the processor further functions as:
a calculation unit configured to calculate a value regarding the plurality of fibers of linear structure; and
a display control unit configured to display information regarding the calculated values on a display unit.

12. The image processing apparatus according to claim 11, wherein the value regarding the plurality of fibers of linear structure is a value of at least one of the number of lines of the plurality of fibers of linear structure, occupancy, and density of the linear structure.

13. The image processing apparatus according to claim 1, wherein the processor further functions as a processing unit configured to emphasize an intensity value of a region having a higher intensity value between a plurality of regions defined by the boundary of the vitreous body in the region located on the vitreous body side of the region regarding the retina and a surface layer of the retina in the detected at least one layer so that the intensity value of the region having the higher intensity value between the plurality of defined regions is emphasized more than a process of emphasizing an intensity value of the region regarding the retina.

14. The image processing apparatus according to claim 1, wherein the detachment region is a posterior vitreous pocket.

15. The image processing apparatus according to claim 1, wherein the image processing apparatus is communicably connected to a tomographic image capturing apparatus including a light reception unit configured to receive light obtained by multiplexing return light from the subject's eye irradiated with measurement light, with reference light corresponding to the measurement light, and
wherein the tomographic image is obtained using based on a light reception result of the light reception unit.

16. An image processing apparatus comprising:
a memory storing a program; and
one or more processors, while executing the program, function as:
a detection unit configured to detect at least one layer of a retina of a subject's eye in a tomographic image of the subject's eye;
a calculation unit configured to calculate a value regarding at least one region except a detachment region the vitreous body of the subject's eye has been detached in a region (a) located on a vitreous body side in the tomographic image and (b) identified using information regarding the detected at least one layer; and
a display control unit configured to display information regarding the calculated value on a display unit.

17. The image processing apparatus according to claim 16, wherein the calculation unit calculates the value by obtaining difference between the vitreous boundary line and the retinal boundary in a specific coordinate.

18. The image processing apparatus according to claim 16, wherein the detachment region is a posterior vitreous pocket.

19. The image processing apparatus according to claim 16, wherein the calculation unit calculates, as the value regarding the at least one region except the detachment region, a value regarding a plurality of fibers of linear structure of the vitreous body in a region located on a vitreous body side in the tomographic image.

20. An image processing method comprising:
  detecting at least one layer of a retina of a subject's eye in a tomographic image of the subject's eye; and
  detecting, using an intensity information regarding the tomographic image, a boundary between a vitreous body of the subject's eye and a detachment region of the vitreous body in a region (a) located on a vitreous body side in the tomographic image (b) identified using information regarding the detected at least one layer.

21. An image processing method comprising:
  detecting at least one layer of a retina of a subject's eye in a tomographic image of the subject's eye;
  calculating a value regarding at least one region except a detachment region of a vitreous body of the subject's eye in a region (a) located on a vitreous body side in the tomographic image and (b) identified using information regarding the detected at least one layer; and
  displaying information regarding the calculated value on a display unit.

22. A non-transitory computer-readable storage medium storing a program for causing a computer to execute steps in the method comprising:
  detecting at least one layer of a retina of a subject's eye in a tomographic image of the subject's eye; and
  detecting, using an intensity information regarding the tomographic image, a boundary between a vitreous body of the subject's eye and a detachment region of the vitreous body in a region (a) located on a vitreous body side in the tomographic image and (b) identified using information regarding the detected at least one layer.

23. A non-transitory computer-readable storage medium storing a program for causing a computer to execute steps in the method comprising:
  detecting at least one layer of a retina of a subject's eye in a tomographic image of the subject's eye;
  calculating a value regarding at least one region except a detachment region of a vitreous body of the subject's eye (a) in a region located on a vitreous body side in the tomographic image and (b) identified using information regarding the detected at least one layer; and
  displaying information regarding the calculated value on a display unit.

24. An image processing apparatus comprising:
  a memory storing a program;
  one or more processors, when executing a program, function as:
  a first detection unit configured to detect at least one layer of a retina of a subject's eye in a tomographic image of the subject's eye; and
  a second detection unit configured to detect, using an intensity information regarding the tomographic image, a plurality of fibers of linear structure of a vitreous body of the subject's eye in the tomographic image.

25. The image processing apparatus according to claim 24, wherein the processor further functions as a display control unit configured to display information regarding a value regarding the plurality of fibers of linear structure on a display unit.

26. The image processing apparatus according to claim 24, wherein the processor further functions as a display control unit configured to display a detection result of the plurality of fibers of linear structure on a display unit.

27. An image processing method comprising:
  detecting at least one layer of a retina of a subject's eye in a tomographic image of the subject's eye; and
  detecting, using an intensity information regarding the tomographic image, a plurality of fibers of linear structure of a vitreous body of the subject's eye in the tomographic image.

28. A non-transitory computer-readable storage medium storing a program for causing a computer to execute steps in the method comprising:
  detecting at least one layer of a retina of a subjet's eye in a tomographic image of the subject's eye; and
  detecting, using an intensity information regarding the tomographic image, a plurality of fibers of linear structure of a vitreous body of the subject's eye in the tomographic image.

* * * * *